(12) United States Patent
Seo et al.

(10) Patent No.: US 11,154,449 B2
(45) Date of Patent: Oct. 26, 2021

(54) CONTROL METHOD AND CONTROL APPARATUS FOR TURNING WALKING

(71) Applicant: Samsung Electronics Co., Ltd., Suwon-si (KR)

(72) Inventors: Keehong Seo, Seoul (KR); Jusuk Lee, Hwaseong-si (KR); Jun-Won Jang, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 309 days.

(21) Appl. No.: 15/901,256

(22) Filed: Feb. 21, 2018

(65) Prior Publication Data

US 2019/0142681 A1 May 16, 2019

(30) Foreign Application Priority Data

Nov. 10, 2017 (KR) .................. 10-2017-0149689

(51) Int. Cl.
*A61H 3/00* (2006.01)
*A61B 5/103* (2006.01)
*A61F 5/01* (2006.01)
*A61B 5/11* (2006.01)
(Continued)

(52) U.S. Cl.
CPC .............. *A61H 3/00* (2013.01); *A61B 5/1038* (2013.01); *A61B 5/1121* (2013.01);
(Continued)

(58) Field of Classification Search
CPC .. A61H 3/00; A61H 1/0244; A61H 2201/165; A61H 2201/5084; A61H 2201/5061; A61H 2201/1671; A61H 2201/1628; A61H 2201/5069; A61H 2201/5007; A61H 2230/00; A61H 2003/007; A61H 1/0237; A61H 2001/0211; A61H 1/0262; A61B 5/4851; A61B 5/6811; A61B 5/1121; A61B 5/1038; A61B 5/1123; A61B 2562/0247; A61B 2562/0219; A61B 2562/0223;
(Continued)

(56) References Cited

U.S. PATENT DOCUMENTS

2010/0114332 A1  5/2010  Ashihara et al.
2011/0295384 A1* 12/2011  Herr .......................... A61F 2/68
                                                    623/24
(Continued)

FOREIGN PATENT DOCUMENTS

JP       5934971 B2      6/2016
KR    10-0949955 B1      3/2010
(Continued)

OTHER PUBLICATIONS

Extended European Search Report issued by the European Patent Office dated Mar. 20, 2019 for the corresponding EP Patent Application No. 18189756.2.

*Primary Examiner* — Jan Christopher L Merene
*Assistant Examiner* — Arielle Wolff
(74) *Attorney, Agent, or Firm* — Harness, Dickey & Pierce, P.L.C.

(57) ABSTRACT

A control method and apparatus for a turning walking receives sensor information, recognizes a turning walking of a user based on the sensor information, and adjusts at least one control parameter to assist the turning walking.

35 Claims, 21 Drawing Sheets

(51) Int. Cl.
   *G16H 20/30* (2018.01)
   *B25J 9/00* (2006.01)
   *A61H 1/02* (2006.01)
   *A61B 5/00* (2006.01)
   *A61F 2/68* (2006.01)

(52) U.S. Cl.
   CPC .......... *A61B 5/4851* (2013.01); *A61B 5/6811* (2013.01); *A61F 2/68* (2013.01); *A61F 5/0102* (2013.01); *A61H 1/0237* (2013.01); *A61H 1/0244* (2013.01); *B25J 9/0006* (2013.01); *G16H 20/30* (2018.01); *A61B 5/1123* (2013.01); *A61B 2562/0219* (2013.01); *A61B 2562/0223* (2013.01); *A61B 2562/0247* (2013.01); *A61F 2005/0155* (2013.01); *A61H 2003/007* (2013.01); *A61H 2201/165* (2013.01); *A61H 2201/1628* (2013.01); *A61H 2201/1671* (2013.01); *A61H 2201/5007* (2013.01); *A61H 2201/5061* (2013.01); *A61H 2201/5069* (2013.01); *A61H 2201/5084* (2013.01); *A61H 2230/00* (2013.01)

(58) Field of Classification Search
   CPC ........... B25J 9/0006; B25J 9/16; G16H 20/30; A61F 2005/0155; A61F 2/68; A61F 5/0102
   See application file for complete search history.

(56) References Cited

U.S. PATENT DOCUMENTS

| | | |
|---|---|---|
| 2012/0095373 A1 | 4/2012 | Hirata et al. |
| 2013/0237884 A1* | 9/2013 | Kazerooni ............... A61H 3/00 601/34 |
| 2014/0212243 A1 | 7/2014 | Yagi et al. |
| 2016/0106616 A1* | 4/2016 | Kim .................... A61B 5/6828 623/25 |
| 2016/0184985 A1* | 6/2016 | Shim ..................... B25J 9/1671 623/32 |
| 2017/0143573 A1 | 5/2017 | Boulanger |
| 2017/0273853 A1 | 9/2017 | Nagata et al. |
| 2018/0055711 A1 | 3/2018 | Choi et al. |
| 2019/0151184 A1* | 5/2019 | Murakami ........... A61H 1/0244 |

FOREIGN PATENT DOCUMENTS

| | | |
|---|---|---|
| KR | 10-2010-0090395 A | 8/2010 |
| KR | 10-2016-0031246 A | 3/2016 |
| KR | 10-2016-0090088 A | 7/2016 |
| KR | 10-2017-0055255 A | 5/2017 |
| KR | 10-2017-0082836 A | 7/2017 |

\* cited by examiner

500

CONTROL METHOD AND CONTROL APPARATUS FOR TURNING WALKING

CROSS-REFERENCE TO RELATED APPLICATION

This application claims under 35 U.S.C. § 119 to Korean Patent Application No. 10-2017-0149689, filed on Nov. 10, 2017, in the Korean Intellectual Property Office, the entire contents of which are incorporated herein by reference in their entirety.

BACKGROUND

1. Field

At least one example embodiment relates to a walking assistance method and/or apparatus. For example, at least some example embodiments relate to a control method and/or control apparatus to assist a user with performing a turning operation while walking.

2. Description of the Related Art

With the onset of rapidly aging societies, an increasing number of people may experience inconvenience and/or pain from joint problems. Thus, there may be a growing interest in walking assistance apparatuses enabling the elderly and/or patients having joint problems to walk with less effort. Further, motion assistance apparatuses increasing muscular strength of users for military purposes are being developed.

A difference between left and right assistance forces for each walking phase, a step length, and a magnitude of a torque in a straight walking period when the user is performing a straight walking operation in a relatively straight line may differ from those in a turning walking period when the user is performing a turning operation. Conventionally, a walking assistance apparatus may not recognize a change from the straight walking operation to the turning walking operation such that the magnitude of the torque in the turning walking period may be controlled to be equal to that in the straight walking period, such that it may be difficult to perform a smooth direction change in the turning walking period.

SUMMARY

Some example embodiments relate to a control method.

In some example embodiments, the control method may include receiving sensor information; recognizing whether a user is performing a turning operation while walking based on the sensor information; and adjusting at least one control parameter to assist the turning operation, if the user is performing the turning operation.

In some example embodiments, the recognizing comprises: tracking a variable component based on the sensor information, the variable component varying in response to the walking; and determining whether the user is performing the turning operation based on the variable component.

In some example embodiments, the determining whether the user is performing the turning operation comprises: extracting a representative component from the variable component; determining whether a variance in the representative component is maintained within a set range; and determining that the user is performing the turning operation, if the variance exceeds the set range.

In some example embodiments, the variable component includes one or more of a direction that a body of the user faces during the walking and a direction that a pelvis of the user faces during the walking.

In some example embodiments, the variable component includes a first variable component and a second variable component, the first variable component corresponding to a motion of a left hip joint of the user, and the second variable component corresponding to a motion of a right hip joint of the user, and wherein the determining whether the user is performing the turning operation comprises: determining whether a variance in the first variable component and a variance in the second variable component are symmetric; and determining that the user is performing the turning operation, if the variance in the first variable component and the variance in the second variable component are asymmetric.

In some example embodiments, the adjusting the at least one control parameter comprises: determining a gain for the at least one control parameter to assist the turning operation; and applying the gain to the at least one control parameter.

In some example embodiments, the at least one control parameter includes one or more of a hip joint torque for each walking phase, an ankle joint torque for each walking phase, a knee joint torque for each walking phase, and a foot sole torque for each walking phase.

In some example embodiments, the control method further includes recognizing a turning direction associated with the turning operation based on the sensor information, wherein the adjusting the at least one control parameter comprises adjusting the at least one control parameter based on the turning direction.

In some example embodiments, the recognizing the turning direction comprises: recognizing the turning direction based on a z-axial rotation angle of a body part from which the sensor information is obtained.

In some example embodiments, when the recognizing the turning direction recognizes the turning direction as a left turn direction, the adjusting of the at least one control parameter based on the turning direction comprises: reducing a swing phase torque of a left hip joint of the user; and reducing a stance phase torque of a right hip joint of the user.

In some example embodiments, when the recognizing the turning direction recognizes the turning direction as a right turn direction, the adjusting of the at least one control parameter based on the turning direction comprises: reducing a stance phase torque of a left hip joint of the user; and reducing a swing phase torque of a right hip joint of the user.

In some example embodiments, when the recognizing the turning direction recognizes the turning direction as a left turn direction, the adjusting of the at least one control parameter based on the turning direction comprises: reducing a push-off phase torque of a right ankle joint of the user.

In some example embodiments, when the recognizing the turning direction recognizes the turning direction as a right turn direction, the adjusting of the at least one control parameter based on the turning direction comprises: reducing a push-off phase torque of a left ankle joint of the user.

In some example embodiments, the control method further includes recognizing a turning degree of the user based on the sensor information, wherein the adjusting the at least one control parameter comprises adjusting the at least one control parameter based on the turning degree.

In some example embodiments, the adjusting of the at least one control parameter comprises: adjusting a gain for the at least one control parameter based on the turning degree.

In some example embodiments, the receiving of the sensor information comprises: receiving the sensor information from one or more of an inertial sensor, an azimuth sensor, a geomagnetic sensor, and a foot sole contact sensor.

Some example embodiments relate to a non-transitory computer-readable medium comprising computer readable instructions to cause a computer to receive sensor information; recognize whether a user is performing a turning operation while walking based on the sensor information; and adjust at least one control parameter to assist the turning operation, if the user is performing the turning operation.

Some example embodiments relate to a control apparatus.

In some example embodiments, the control apparatus includes a communication interface configured to receive sensor information; and a processor configured to, recognize whether a user is performing a turning operation while walking based on the sensor information, and adjust at least one control parameter to assist the turning operation, if the user is performing the turning operation.

In some example embodiments, the processor is configured to, track a variable component based on the sensor information, the variable component varying in response to the walking, and determine whether the user is performing the turning operation based on the variable component.

In some example embodiments, the processor is configured to, extract a representative component from the variable component, determine whether a variance in the representative component is maintained within a set range, and determine that the user is performing the turning operation, if the variance exceeds the set range.

In some example embodiments, the variable component includes one or more of a direction that a body of the user faces during the walking and a direction that a pelvis of the user faces during the walking.

In some example embodiments, the variable component includes a first variable component and a second variable component, the first variable component corresponding to a motion of a left hip joint of the user, and the second variable component corresponding to a motion of a right hip joint of the user, and wherein the processor is configured to, determine whether a variance in the first variable component and a variance in the second variable component are symmetric, and determine that the user is performing the turning operation, if the variance in the first variable component and the variance in the second variable component are asymmetric.

In some example embodiments, the processor is configured to, determine a gain for the at least one control parameter to assist the turning operation, and apply the gain to the at least one control parameter.

In some example embodiments, the at least one control parameter includes one or more of a hip joint torque for each walking phase, an ankle joint torque for each walking phase, a knee joint torque for each walking phase, and a foot sole torque for each walking phase.

In some example embodiments, the processor is configured to, recognize a turning direction associated with the turning operation based on the sensor information, and adjust the at least one control parameter based on the turning direction.

In some example embodiments, the processor is configured to recognize the turning direction based on a z-axial rotation angle of a body part from which the sensor information is obtained.

In some example embodiments, the processor is configured to, when the turning direction is left, reduce a swing phase torque of a left hip joint of the user, and reduce a stance phase torque of a right hip joint of the user.

In some example embodiments, the processor is configured to, when the turning direction is right, reduce a stance phase torque of a left hip joint of the user, and reduce a swing phase torque of a right hip joint of the user.

In some example embodiments, the processor is configured to, when the turning direction is left, reduce a push-off phase torque of a right ankle joint of the user.

In some example embodiments, the processor is configured to, when the turning direction is right, reduce a push-off phase torque of a left ankle joint of the user.

In some example embodiments, the processor is configured to, recognize a turning degree of the user based on the sensor information, and adjust the at least one control parameter based on the turning degree.

In some example embodiments, the processor is configured to adjust a gain for the at least one control parameter based on the turning degree.

In some example embodiments, the communication interface is configured to receive the sensor information from one or more of an inertial sensor, an azimuth sensor, a geomagnetic sensor, and a foot sole contact sensor.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
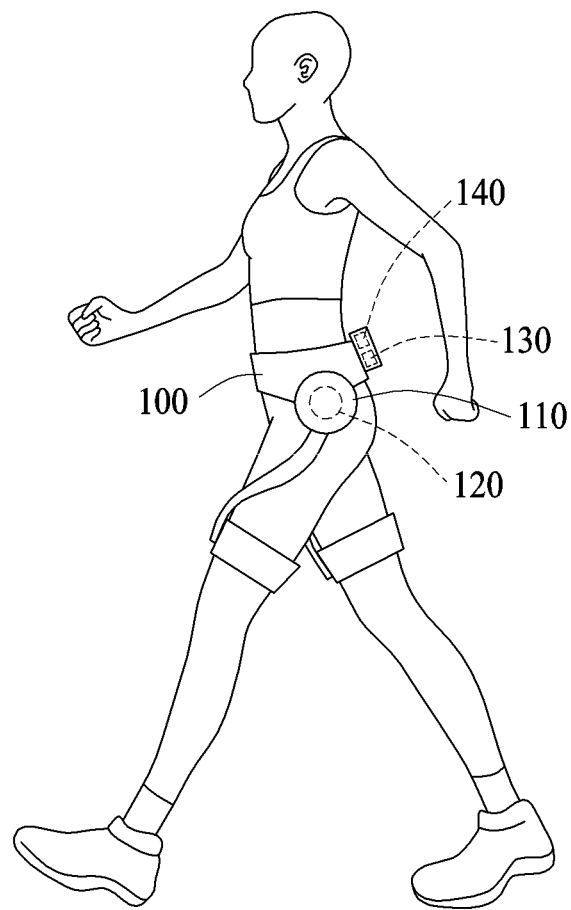
FIGS. 1 and 2 illustrate a configuration of a walking assistance apparatus according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Figure 2:
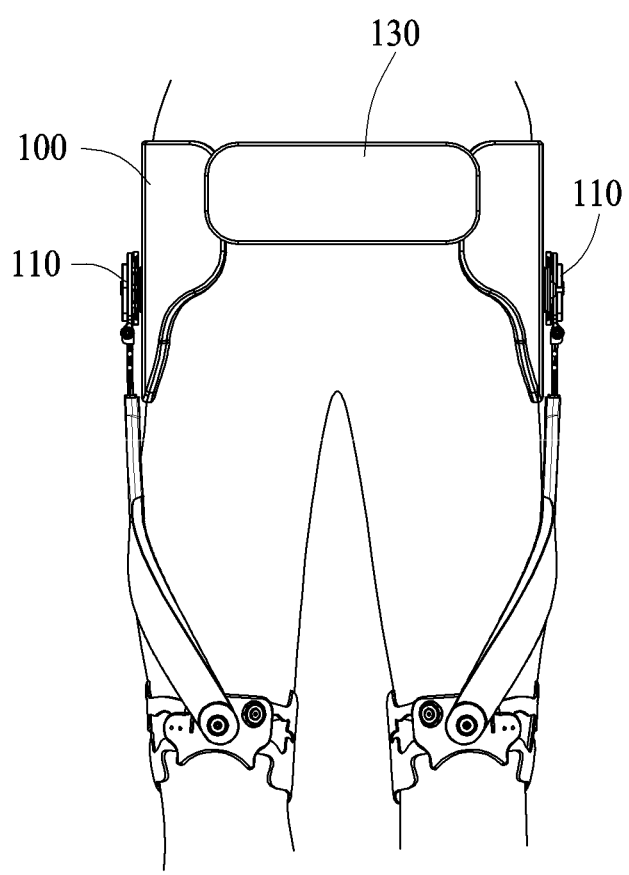

FIGS. 1 and 2 illustrate a configuration of a walking assistance apparatus according to at least one example embodiment.

Referring to FIGS. 1 and 2, a walking assistance apparatus 100 may assist a walking of a user. The walking assistance apparatus 100 may be a wearable device.

Although FIG. 1 illustrates a hip-type walking assistance apparatus, the type of the walking assistance apparatus 100 is not limited thereto. The walking assistance apparatus may support an entire pelvic limb or a portion of a pelvic limb. The walking assistance apparatus may be one of a walking assistance apparatus that supports a portion of a pelvic limb, a walking assistance apparatus that supports up to a knee, a walking assistance apparatus that supports up to an ankle, and a walking assistance apparatus that supports an entire body.

The examples set forth hereinafter may be applicable to the hip-type walking assistance apparatus. However, at least one example embodiment is not limited thereto. The examples may also be applicable to all various types of apparatuses that assist a walking of a user, for example, an active prosthetic leg.

The walking assistance apparatus 100 may include a driver 110, a sensor 120, an inertial measurement unit (IMU) sensor 130, and a controller 140.

The driver 110 may provide a driving force to a hip joint of the user. The driver 110 may be positioned at a right hip portion and/or a left hip portion of the user. In an example, the driver 110 may provide the driving force to left and right knee joints and left and right ankle joints, in addition to hip joints of the user. The driver 110 may include a motor configured to generate a rotational torque.

The sensor 120 may measure an angle of the hip joint of the user during a walking. Information related to the angle of the hip joint sensed by the sensor 120 may include an angle of the right hip joint, an angle of the left hip joint, a difference between the angles of the hip joints, and a moving direction of the hip joint. In an example, the sensor 120 may measure angles of the left and right knee joints and/or the left and right ankle joints of the user during a walking. For example, the sensor 120 may be included in the driver 110.

The sensor 120 may include a potentiometer. The potentiometer may sense R-axial and L-axial joint angles and R-axial and L-axial joint angular velocities with respect to a walking motion of the user.

The IMU sensor 130 may measure acceleration information and posture information during a walking. The IMU sensor 130 may include a tri-axial gyro sensor, and an acceleration sensor. For example, the IMU sensor 130 may sense tri-directional, for example, X-axial, Y-axial and Z-axial, accelerations and rotation rates, and tri-directional, for example, roll, pitch and yaw, tilt angles with respect to the walking motion of the user. In this example, an orientation of the IMU sensor 130, that is, a direction that a torso of the user faces when viewed from above a head of the user, may be known through the yaw angle. Hereinafter, the direction that the torso of the user faces will be referred to as a "body yaw angle".

The walking assistance apparatus 100 may detect a landing point of a foot of the user based on the acceleration information measured by the IMU sensor 130. A pressure sensor (not shown) may be on a sole of the foot of the user to detect the landing point of the foot of the user.

In addition to the sensor 120 and the IMU sensor 130, the walking assistance apparatus 100 may further include various sensors, for example, an electromyogram (EMG) sensor, configured to sense a change in a biosignal or a quantity of motion of the user with respect to the walking motion.

The controller 140 may include processing circuitry and a memory (not shown).

The controller 140 may further include a communication device, and communicate with an external device using the communication device.

The processing circuitry may be, but not limited to, a processor, Central Processing Unit (CPU), a controller, an arithmetic logic unit (ALU), a digital signal processor, a microcomputer, a field programmable gate array (FPGA), an Application Specific Integrated Circuit (ASIC), a System-on-Chip (SoC), a programmable logic unit, a microprocessor, or any other device capable of performing operations in a defined manner.

The processing circuitry may be configured, through a layout design or execution of computer readable instructions stored in a memory (not shown), as a special purpose computer to control the driver 110 to output an assistance force to assist the walking of the user by recognize a turning walking and adjust at least one control parameter. Therefore, the controller 140 may improve the functioning of the walking assistance apparatus 100 itself by enabling a smooth turning walking in response to the recognition of the turning walking.

The driver 110 may be attached in forward, backward, left and right operating directions of the hip joints to generate a torque to be used to assist the walking, and also attached in forward, backward, left and right operating directions of the knees and/or the ankles. Further, the driver 110 may be attached to each of the hip joints, the knees, and/or the ankles. As described above, a plurality of drivers 110 may be attached to various body parts that require the assistance force to assist the walking of the user.

For example, in the hip-type walking assistance apparatus 100, two drivers 110 may be attached to the left hip and the right hip, and the controller 140 may output a control signal to control the driver 110 to generate the torque. The driver 110 may generate the torque based on the control signal output from the controller 140. The control signal may include, for example, a control parameter, and/or a gain for the control parameter.

In a case in which the magnitude of the torque in the turning walking period is equal to that in the straight walking period, a smooth direction change may be difficult. Therefore, in one or more example embodiments, the controller 140 may control the driver 110 such that there is a difference between left and right assistance forces and a magnitude of a torque in a straight walking period as compared to those in a turning walking period. For example, to recognize a turning walking and assist the turning walking in response to the recognition of the turning walking, the controller 140 may adjust at least one control parameter to enable a smooth turning walking. An example of recognizing the turning walking and adjusting the control parameter will be described further with reference to FIGS. 3 through 18.

Figure 3:
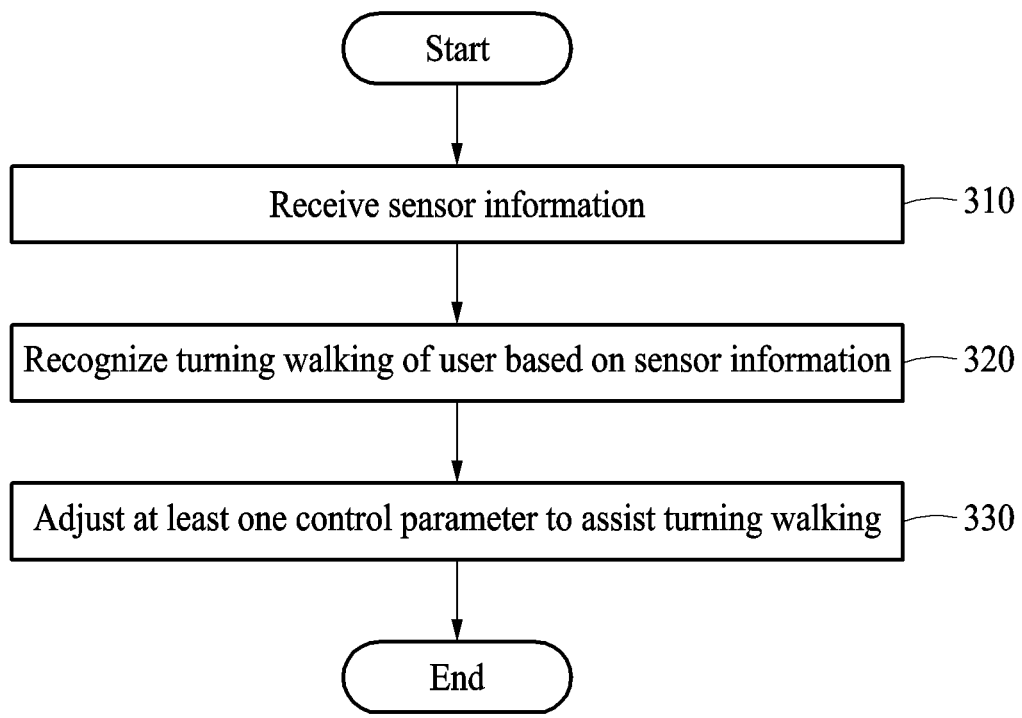
FIG. 3 is a flowchart illustrating a control method for a turning walking according to at least one example embodiment.

FIG. 3 is a flowchart illustrating a control method for a turning walking according to at least one example embodiment.

Referring to FIG. 3, a control apparatus configured to perform turning walking, hereinafter, the "control apparatus", may be the walking assistance apparatus 100 described above, or a separate apparatus for a walking assistance apparatus.

In operation 310, the control apparatus may receive sensor information. The sensor information may be sensed from a body part that is relatively close to a torso of a user, for example, a pelvis, an abdomen, a chest, a back or a head, or a body part that performs a few motions, for example, an arm or a leg. Further, the sensor information may be sensed by any one or any combination of a joint sensor such as a joint angle sensor or a joint acceleration sensor, an inertial sensor, an azimuth sensor, a geomagnetic sensor, a pressure sensor, and a foot sole contact sensor. The joint angle sensor may include a resistive sensor, a capacitive sensor, and a polarization sensor.

The sensor information may include, for example, an angle of a hip joint of the user, an angular velocity of the hip joint, an angular acceleration of the hip joint, an angle of a knee joint, an angular velocity of the knee joint, an angular acceleration of the knee joint, an angle of an ankle joint, an angular velocity of the ankle joint, an angular acceleration of the ankle joint, a magnitude of pressure, and data sensed by the inertial sensor.

For example, the controller 140 may receive the sensor information from one or more of the sensor 120 and the IMU sensor 130.

In operation 320, the control apparatus may recognize a turning walking of the user based on the sensor information. For example, the controller 140 may recognize the user is attempting to turn while walking using the sensor data received from one or more of the sensor 120 and the IMU sensor 130. An example of the control apparatus recognizing the turning walking of the user will be described further with reference to FIGS. 4 through 6.

In some example embodiments, instead of recognizing the turning walking while the turning walking is happening, the controller 140 may receive the sensor information from one or more cameras and/or inertial sensors attached to the head of the user, and predict that the user is going to performing the turning walking based on the sensor information. For example, the user may turn their head and/or eyes in the direction of intended movement at the beginning of the turning walking. The controller 140 may detect this walking intention of the user in advance of the user turning to further improve the smoothness of the turning operation.

In operation 330, the control apparatus may adjust at least one control parameter to assist the turning walking. For example, the controller 140 may adjust at least one of the control parameters in response to recognizing the turning while walking by determining a gain for the at least one control parameter, and applying the gain to the at least one control parameter, thereby adjusting the control parameter.

In one example, in response to recognition of the turning walking, the control apparatus (e.g., the controller, 140) may reduce all torques of drivers of the control apparatus by multiplying all control parameters by the gain, irrespective of a turning direction. In another example, the control apparatus may recognize the turning direction based on the sensor information, and control the at least one control parameter based on the turning direction. In another example, the control apparatus may recognize a turning degree of the user based on the sensor information, and adjust the at least one control parameter based on the turning degree. The turning degree may include, for example, a rotation angle, and/or a rotation angular velocity. In still another example, the control apparatus may adjust the gain for the at least one control parameter based on the turning degree. Examples of the control apparatus adjusting the gain will be described further with reference to FIGS. 7A through 7D.

The control parameter may include, for example, a hip joint torque for each walking phase, an ankle joint torque for each walking phase, a knee joint torque for each walking phase, and a foot sole torque for each walking phase. Walking phases will be described in detail with reference to FIG. 10. Further, examples of the control apparatus adjusting the control parameter will be described further with reference to FIGS. 11 through 14.

In some example embodiments, the adjustment amount of the gain γ may be based on individual parameters associated with the user. For example, the controller 140 may recognize a weight of the user and set the gain to an appropriate level based on the individual parameters. For example, the gain may be initially set based on a reference model, the controller 140 may measure the weight of the user using sensors or may receive input of the same from the user, and may adjust the amount of gain proportional to the excess amount of weight associated with the user beyond the weight associated with a reference model.

Figure 4:
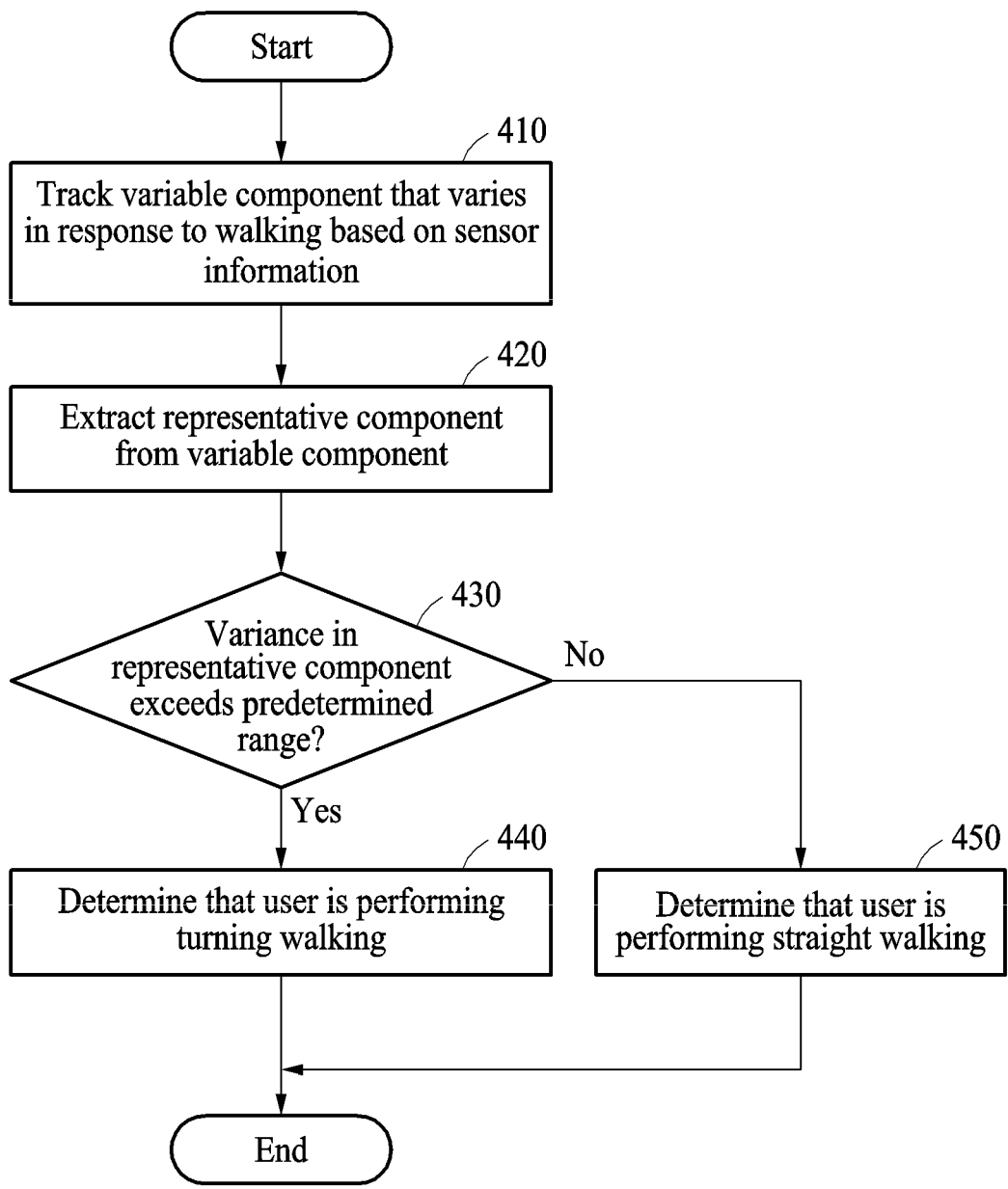
FIG. 4 is a flowchart illustrating an example of recognizing a turning walking according to at least one example embodiment.
Figure 5:
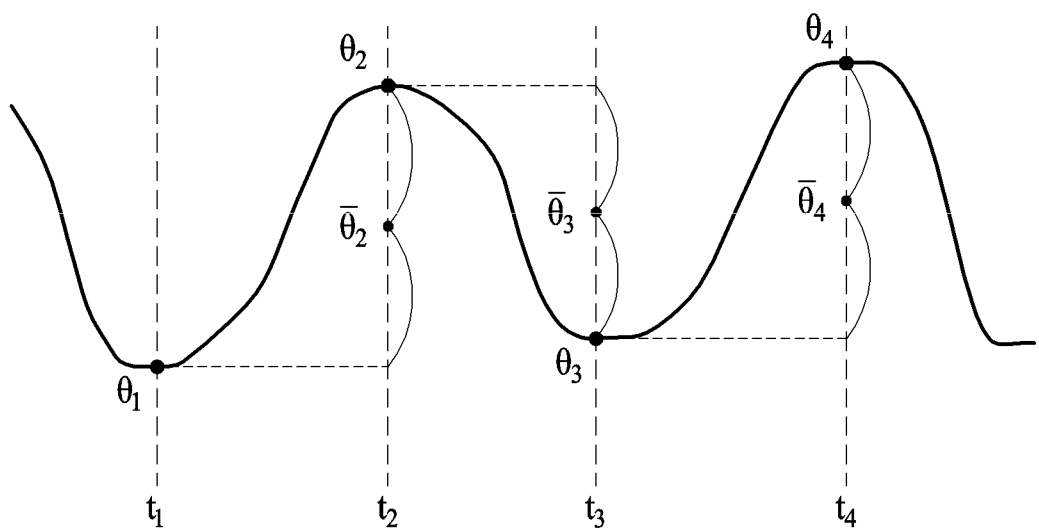
FIG. 5 is a graph illustrating a change in a variable component during a walking of a user according to at least one example embodiment.

FIG. 4 is a flowchart illustrating an example of recognizing a turning walking according to at least one example embodiment, and FIG. 5 is a graph illustrating a change in a variable component during a walking of a user according to at least one example embodiment.

Referring to FIGS. 4 and 5, in operation 410, the control apparatus may track a variable component that varies in response to a walking, based on sensor information. In a graph 500 of FIG. 5, a variable component may indicate a direction that a torso of a user faces during the walking, that is, a body yaw angle, or a direction that a pelvis of the user faces during the walking. The control apparatus may determine whether the user is performing a turning walking based on the variable component.

In operation 420, the control apparatus may extract a representative component from the variable component. For example, the controller 140 may read, from the graph 500 of FIG. 5, values θ1 and θ3 at instances at which the variable component, that is, the body yaw angle, is minimized, for example, times t1 and t3, and values θ2 and θ4 at instances at which the variable component is maximized, for example, times t2 and t4, and extracts median values $\overline{\theta}_2, \overline{\theta}_3, \overline{\theta}_4, \ldots$ thereof as representative components.

In operation 430, the control apparatus may determine whether a variance in the representative component exceeds a desired (or, alternatively, a predetermined) range. For example, the controller 140 may update the median values $\overline{\theta}_2, \overline{\theta}_3, \overline{\theta}_4, \ldots$ in the graph 500 of FIG. 5, and identify an i-th change $\Delta\overline{\theta}_i = \overline{\theta}_i - \overline{\theta}_{i-1}$ of each median value per step by comparing the corresponding median value to a previous median value. In this example, the i-th change $\Delta\overline{\theta}_i$ of each median value per step may correspond to a variance in the representative component.

In response to determining that the variance in the representative component exceeds the desired (or, alternatively, the predetermined) range, in operation 440, the control apparatus may determine that the user is performing a turning walking. For example, in a case in which θ* denotes the desired (or, alternatively, the predetermined) range or a threshold, the controller 140 may determine that the user is performing a turning walking if $|\Delta\overline{\theta}_i| > \theta^*$.

In response to determining that the variance in the representative component is maintained within the desired (or, alternatively, the predetermined) range, in operation 450, the control apparatus may determine that the user is performing a straight walking. For example, if $|\Delta\overline{\theta}_i| \leq \theta^*$, the controller 140 may determine that the user is performing a straight walking. In this example, the desired (or, alternatively, the predetermined) range or threshold may be determined empirically through experimentation.

In response to determining that the user is performing a turning walking, the control apparatus may determine a turning direction to be left or right based on a sign of $\Delta\overline{\theta}_i$. For example, in a case in which the body yaw angle is defined to increase in response to a left turning, the controller 140 may determine the turning direction to be left if $\Delta\overline{\theta}_i > 0$, and determine the turning direction to be right if $\Delta\overline{\theta}_i < 0$.

Figure 6:
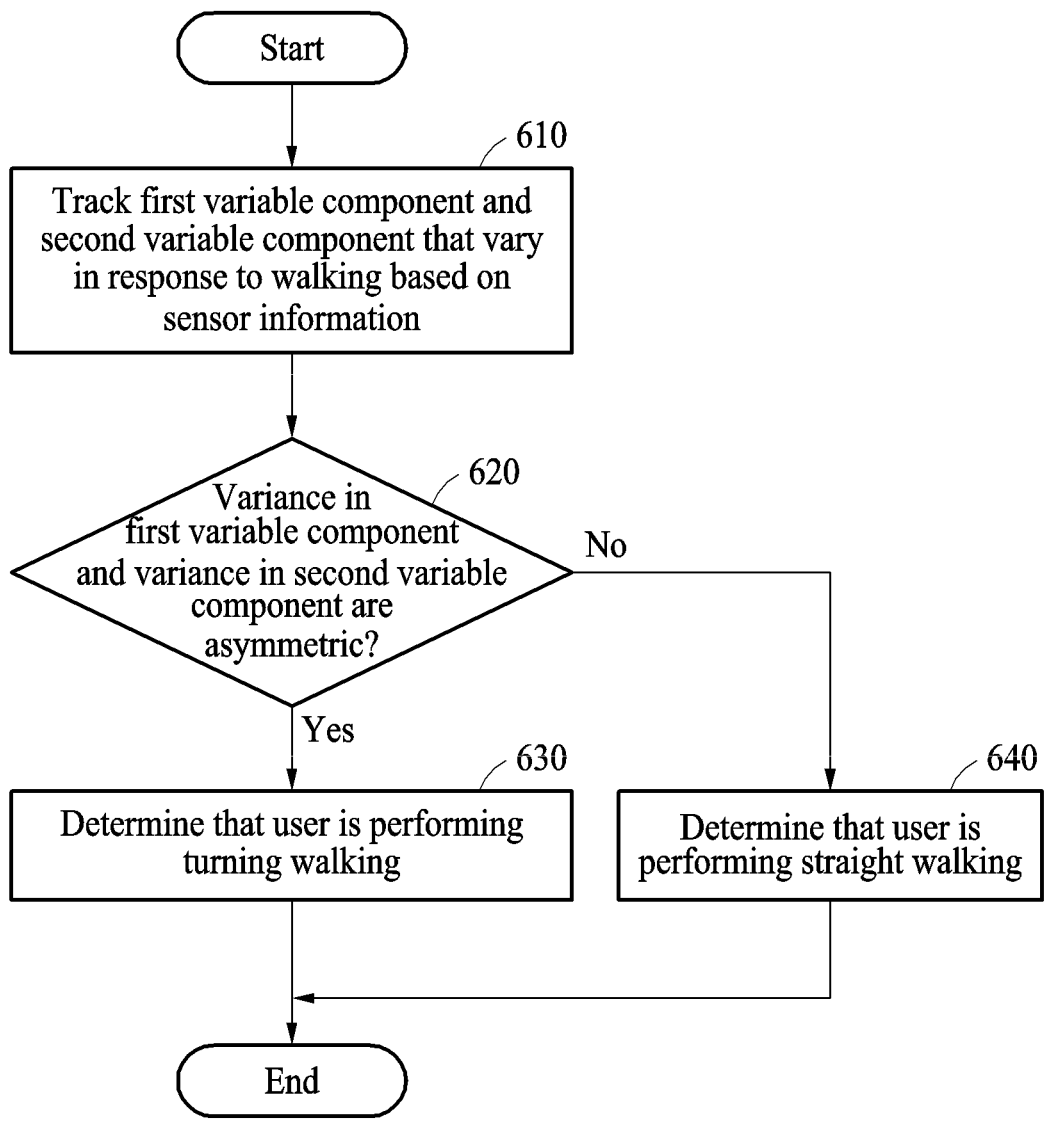
FIG. 6 is a flowchart illustrating an example of recognizing a turning walking according to at least one example embodiment.

FIG. 6 is a flowchart illustrating an example of recognizing a turning walking according to at least one example embodiment.

Referring to FIG. 6, in operation 610, the control apparatus may track a first variable component and a second variable component that vary in response to a walking, based on sensor information. For example, the first variable component may correspond to a motion of a left joint of a user, and the second variable component may correspond to a motion of a right joint of the user.

The control apparatus may recognize whether the user is performing a turning walking by determining whether a variance in the first variable component and a variance in the second variable component are symmetric.

For example, in operation 620, the controller 140 may determine whether the variance in the first variable component and the variance in the second variable component are asymmetric. In response to determining that the variance in the first variable component and the variance in the second variable component are asymmetric, in operation 630, the controller 140 may determine that the user is performing a turning walking. Likewise, in response to determining that the variance in the first variable component and the variance in the second variable component are not asymmetric, that is, the variance in the first variable component and the variance in the second variable component are symmetric, in operation 640, the controller 140 may determine that the user is performing a straight walking.

For example, in a case in which the user is performing a left turning walking, a left leg of the user on an inner side of a turning direction may relatively narrow a step length in comparison to a right leg on an outer side of the turning direction, thereby enabling a smooth turning walking. In a case in which the user is performing a right turning walking, the right leg of the user on an inner side of a turning direction may relatively narrow a step length in comparison to the left leg on an outer side of the turning direction. By differing a step length of one leg as described above, there may arise a difference between the variance in the first variable component and the variance in the second variable component. The control apparatus may distinguish between a turning walking and a straight walking based on an asymmetry between the variance in the first variable component and the variance in the second variable component.

FIGS. 7A through 7D illustrate examples of determining a gain for a control parameter according to at least one example embodiment.

In a case of determining a torque to assist a turning walking, a degree of a straight walking and a degree of a turning walking may be expressed using a gain for a control parameter, without distinguishing between the straight walking and the turning walking. The gain may have a value of a real number greater than or equal to "0" and less than or equal to "1". The torque may be continuously adjusted using the gain based on whether a user is performing a straight walking or a turning walking.

To assist the turning walking, the control apparatus may determine a gain γ with respect to a torque calculated in a turning walking period, and apply the gain to a control parameter. The control apparatus may determine the gain to change based on a variance $\Delta\overline{\theta}_i$ in a representative component of the tracked variable component.

Figure 7A:
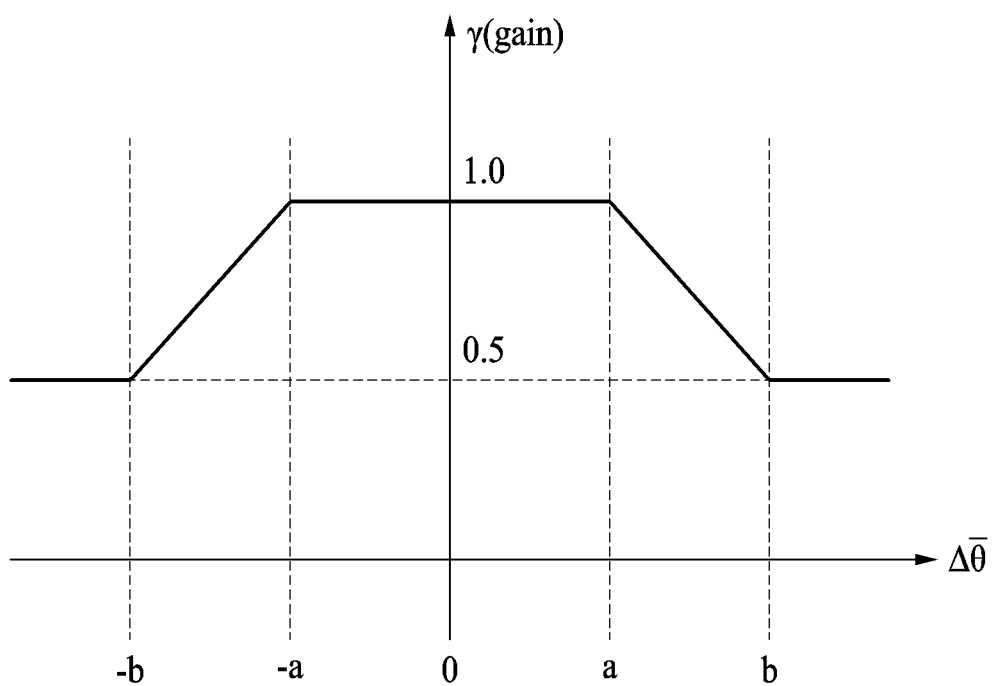
FIGS. 7A through 7D illustrate examples of determining a gain for a control parameter according to at least one example embodiment.

Referring to FIG. 7A, in a graph of FIG. 7A, a first threshold with respect to the variance $\Delta\overline{\theta}_i$ in the representative component may be ±a, and a second threshold may be ±b. In this example, the first threshold may correspond to a variance, for example, ±7 degrees, which may be regarded as a straight walking, and the second threshold may correspond to a variance which may be regarded as a turning walking.

If the variance $\Delta\bar{\theta}_i$ in the representative component is within ±a, the control apparatus may determine the gain γ to be "1". If the variance $\Delta\bar{\theta}_i$ in the representative component exceeds ±b, the control apparatus may determine the gain γ to be "0.5".

If the variance $\Delta\bar{\theta}_i$ in the representative component is in remaining regions, for example, a region in which the variance $\Delta\bar{\theta}_i$ in the representative component is greater than −b and less than −a, and a region in which the variance $\Delta\bar{\theta}_i$ in the representative component is greater than a and less than b, the control apparatus may determine the gain γ to be a linear value between "0.5" and "1" such that the gain γ may not change suddenly.

Figure 7B:
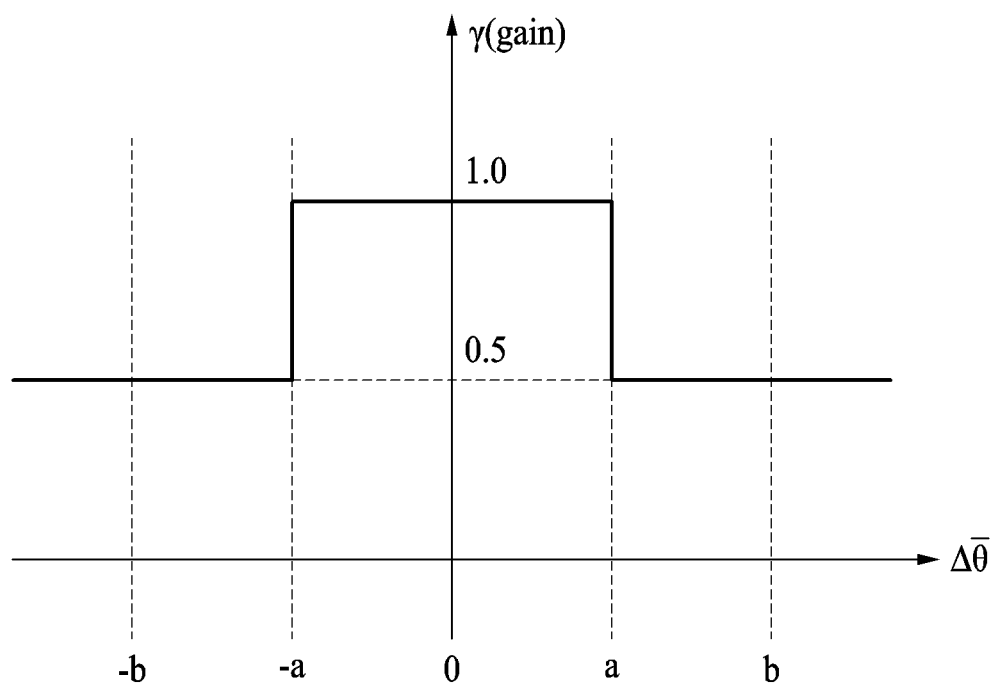

Referring to FIG. 7B, in a graph of FIG. 7B, if the variance $\Delta\bar{\theta}_i$ in the representative component is within ±a, the control apparatus may determine the gain γ to be "1". In addition, if the variance $\Delta\bar{\theta}_i$ in the representative component exceeds ±a, the control apparatus may determine the gain γ to be "0.5".

Figure 7C:
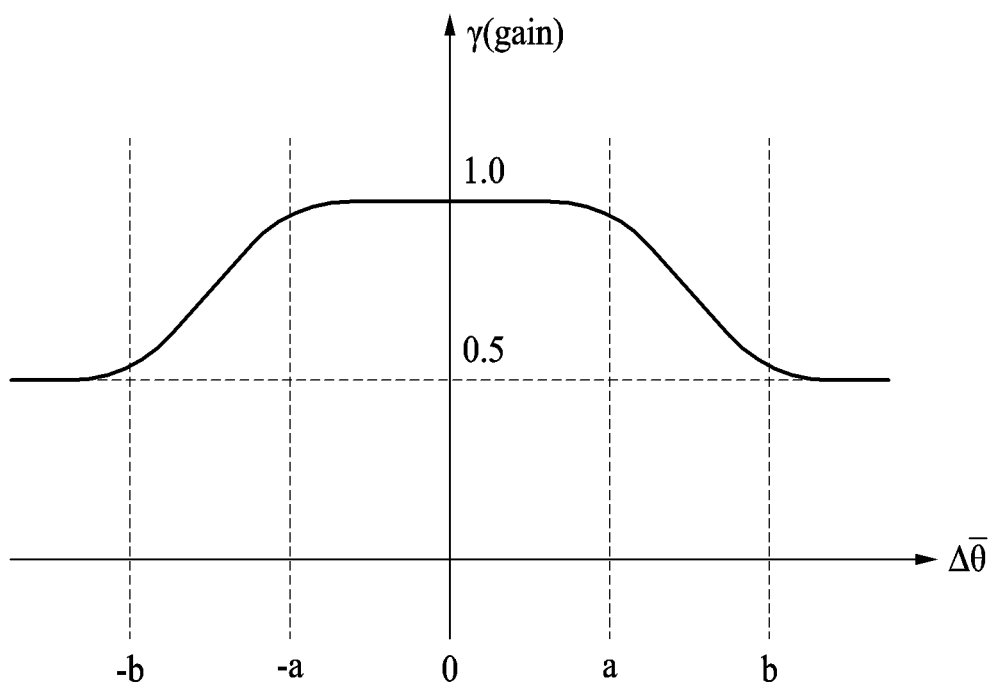

Referring to FIG. 7C, in a graph of FIG. 7C, if the variance $\Delta\bar{\theta}_i$ in the representative component is within ±a, the control apparatus may determine the gain γ to be "1". If the variance $\Delta\bar{\theta}_i$ in the representative component exceeds ±a, the control apparatus may determine the gain γ to be a value that gently decreases from "1" to "0.5".

Figure 7D:
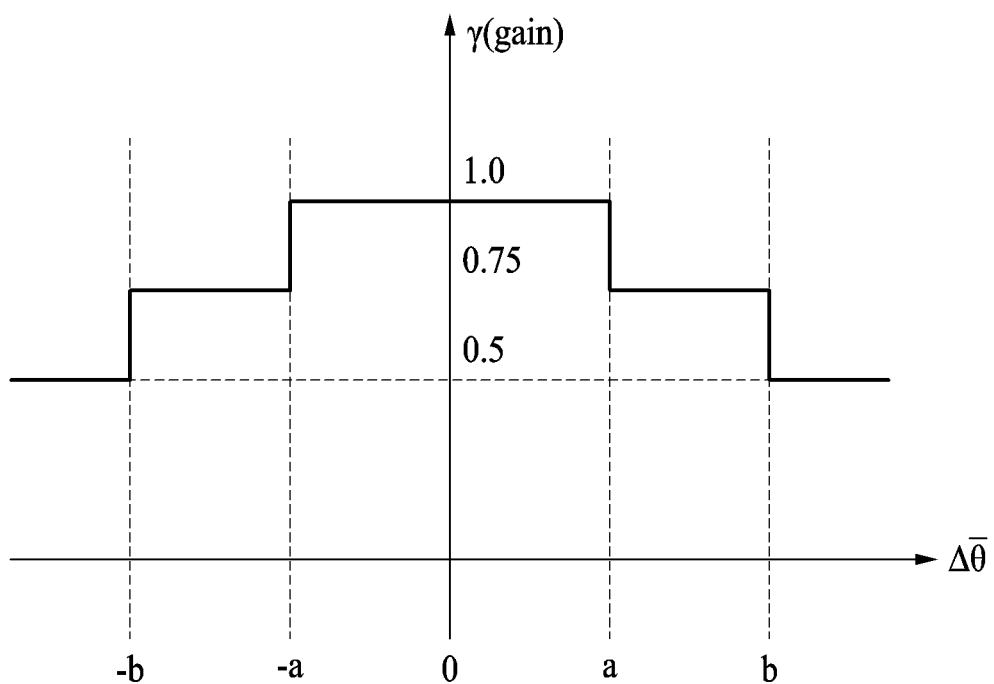

Referring to FIG. 7D, in a graph of FIG. 7D, if the variance $\Delta\bar{\theta}_i$ in the representative component is within ±a, the control apparatus may determine the gain γ to be "1". If the variance $\Delta\bar{\theta}_i$ in the representative component exceeds ±b, the control apparatus may determine the gain γ to be "0.5". If the variance $\Delta\bar{\theta}_i$ in the representative component is in remaining regions, for example, a region in which the variance $\Delta\bar{\theta}_i$ in the representative component is greater than −b and less than −a, and a region in which the variance $\Delta\bar{\theta}_i$ in the representative component is greater than a and less than b, the control apparatus may determine the gain γ to be "0.75".

Figure 8:
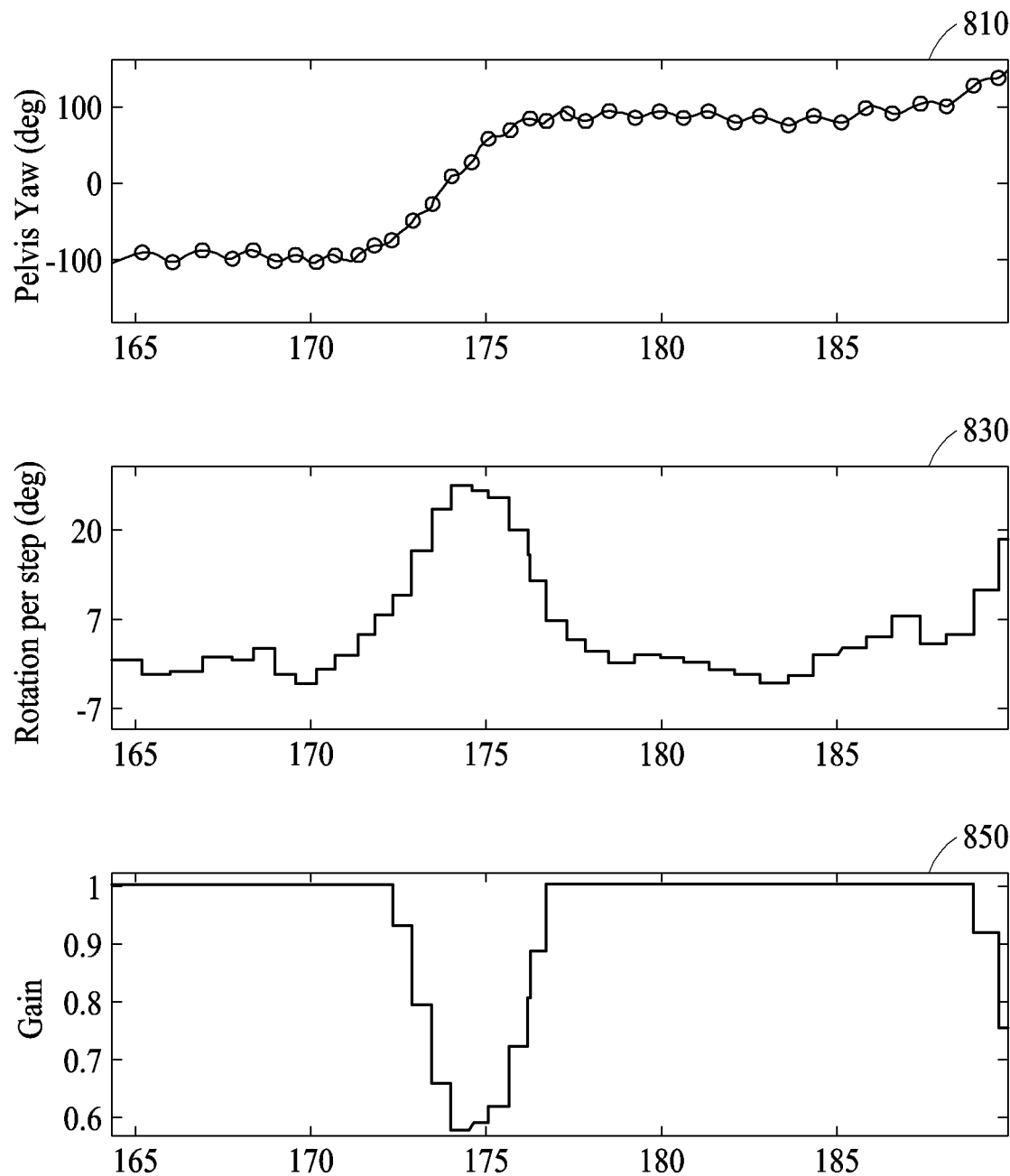
FIG. 8 illustrates a relationship among a variable component, a variance in the variable component, and a gain in a turning walking period with respect to a turning walking according to at least one example embodiment.

FIG. 8 illustrates a relationship among a variable component, a variance in the variable component, and a gain in a turning walking period with respect to a turning walking according to at least one example embodiment.

Referring to FIG. 8, a graph 810 may show a change in a pelvis yaw angle $\theta_i$ with respect to a turning walking of a user or a median value $\bar{\theta}_i$ of a pelvis yaw angle determined from a value at an instant at which the pelvis yaw angle is maximized and a value at an instant at which the pelvis yaw angle is minimized. In the graph 810, a period during which the value $\bar{\theta}_i$ changes, for example, a period between 170 seconds and 175 seconds, may correspond to a turning walking period.

A graph 830 may show a rotation per step $\Delta\bar{\theta}_i$. The rotation per step may correspond to a rate of change in the pelvis yaw angle $\theta_i$ or the medium value $\bar{\theta}_i$ of the pelvis yaw angle. For example, the rotation per step may be close to "0" in a straight walking period, and increase to "20" or higher in a turning walking period.

In this example, a value of a gain γ, which is a parameter to determine whether a user is performing a turning walking, is represented in a graph 850. In the graph 850, the gain γ may be maintained at "1" in the straight walking period, and may decrease when the rotation per step increases to be greater than or equal to a desired (or, alternatively, a predetermined) value, for example, 7 degrees.

In response to recognition of a turning walking, the control apparatus (e.g., the controller 140) may reduce a magnitude of a torque by multiplying all control parameters by the gain, thereby enabling a smoother torque control and a smoother direction change in the turning walking period.

Figure 9:
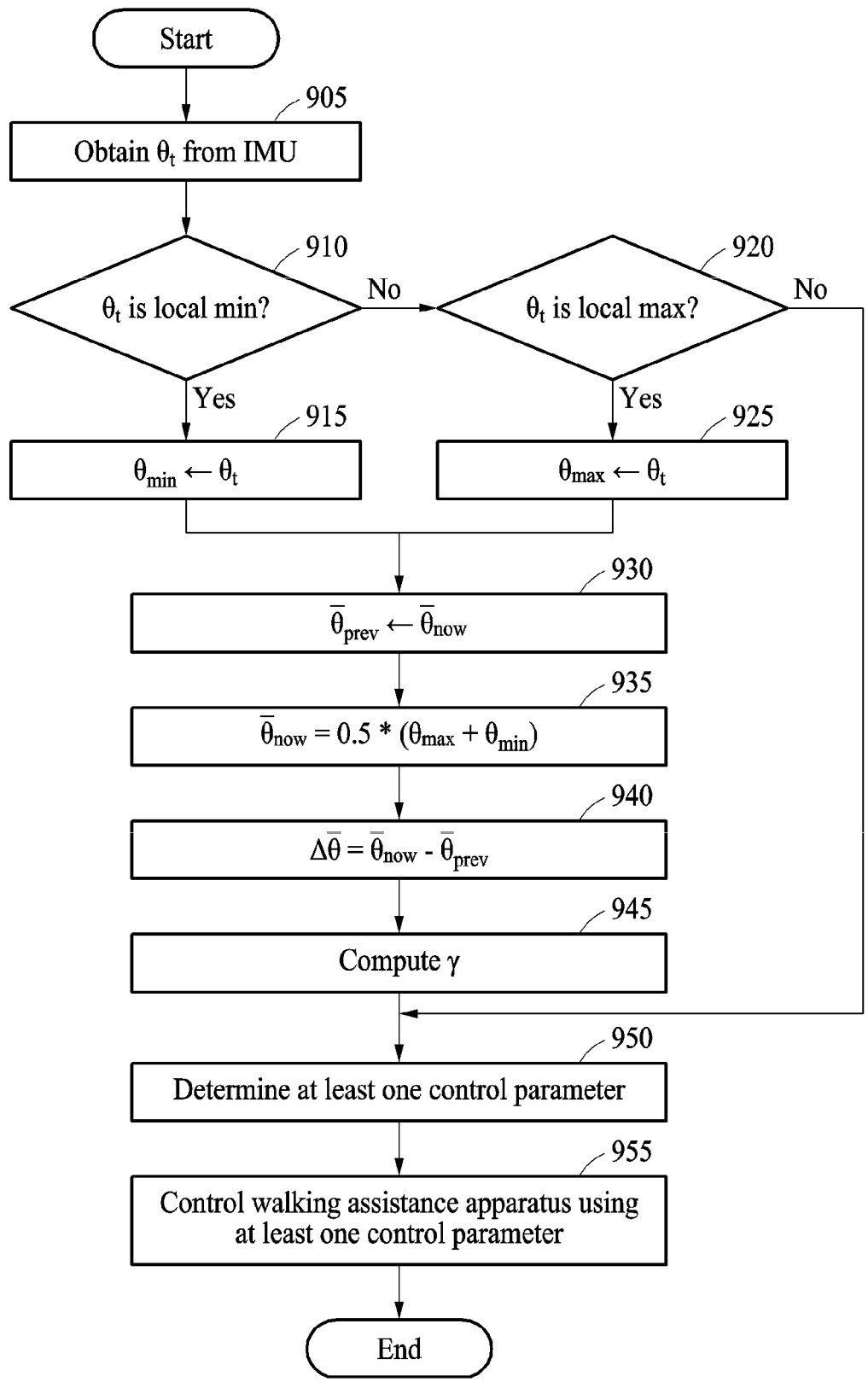
FIG. 9 is a flowchart illustrating an example of controlling a walking assistance apparatus according to at least one example embodiment.

FIG. 9 is a flowchart illustrating an example of controlling a walking assistance apparatus according to at least one example embodiment.

Referring to FIG. 9, in operation 905, a walking assistance apparatus (e.g., the controller 140) may acquire sensor information $\theta_t$ from an IMU sensor (e.g., the IMU sensor 130).

In operation 910, the walking assistance apparatus (e.g., the controller 140) may determine whether the sensor information $\theta_t$ is a smallest value of pieces of sensor information. In response to determination that the sensor information $\theta_t$ is a smallest value, in operation 915, the walking assistance apparatus (e.g., the controller 140) may determine the sensor information $\theta_t$ to be a minimum value $\theta_{min}$.

In response to determining that the sensor information $\theta_t$ is not a smallest value of the pieces of sensor information, in operation 920, the walking assistance apparatus (e.g., the controller 140) may determine whether the sensor information $\theta_t$ is a greatest value of the pieces of sensor information. In response to determining that the sensor information $\theta_t$ is not a greatest value of the pieces of sensor information, in operation 950, the walking assistance apparatus (e.g., the controller 140) may determine at least one control parameter. In operation 955, the walking assistance apparatus (e.g., the controller 140) may control the walking assistance apparatus using the at least one control parameter.

In response to determining that the sensor information $\theta_t$ is a greatest value of the pieces of sensor information, in operation 925, the walking assistance apparatus (e.g., the controller 140) may determine the sensor information $\theta_t$ to be a maximum value $\theta_{max}$.

In operation 930, the walking assistance apparatus (e.g., the controller 140) may set a previous rate of change $\bar{\theta}_{prev}$ based on a current rate of change $\bar{\theta}_{now}$ in the sensor information. In operation 935, the walking assistance apparatus (e.g., the controller 140) may determine a mean value of the minimum value $\theta_{min}$ and the maximum value $\theta_{max}$ to be the current rate of change $\bar{\theta}_{now}$.

In operation 940, the walking assistance apparatus (e.g., the controller 140) may calculate a difference $\Delta\bar{\theta}$ between the current rate of change $\bar{\theta}_{now}$ and the previous rate of change $\bar{\theta}_{prev}$.

In operation 945, the walking assistance apparatus (e.g., the controller 140) may calculate a gain γ corresponding to $\Delta\bar{\theta}$. For example, the walking assistance apparatus may calculate the gain γ corresponding to $\Delta\bar{\theta}$ using the methods described through FIGS. 7A through 7D.

In operation 950, the walking assistance apparatus (e.g., the controller 140) may determine at least one control parameter by applying the calculated gain.

In operation 955, the walking assistance apparatus (e.g., the controller 140) may control the walking assistance apparatus using the at least one control parameter.

Figure 10:
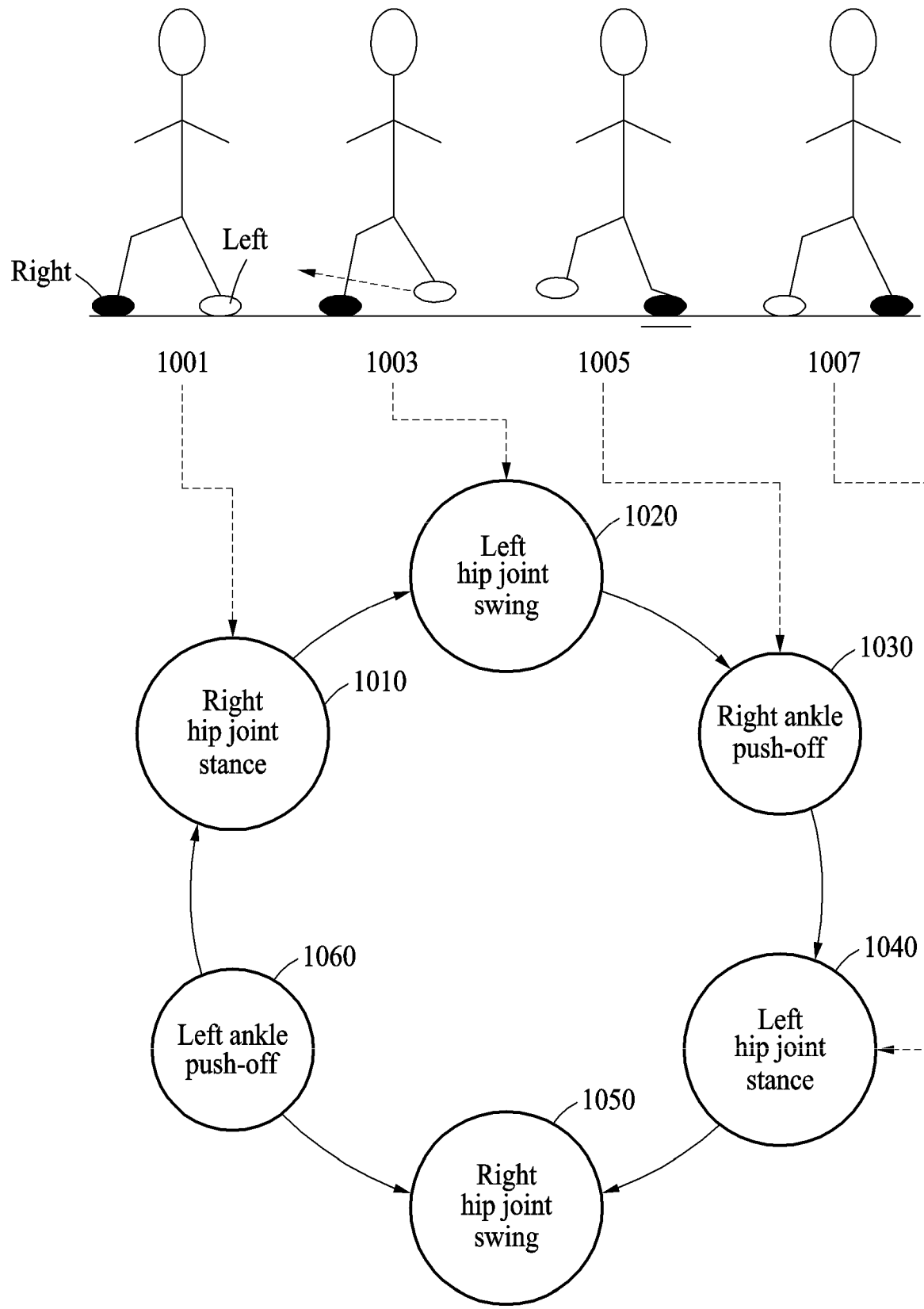
FIG. 10 illustrates transitions between walking phases according to at least one example embodiment.

FIG. 10 illustrates transitions between walking phases according to at least one example embodiment.

Referring to FIG. 10, walking motions 1001, 1003, 1005 and 1007 of a user during a walking, and walking phases 1010, 1020, 1030, 1040, 1050 and 1060 are illustrated.

During a walking, a left leg and a right leg may move symmetrically, and thus the left leg and the right leg may have the same or similar walking cycles. For example, a walking cycle may be defined as a cycle from an instant at which a first leg is in contact with the ground to an instant at which the first leg is in contact with the ground again.

The walking motions 1001, 1003, 1005 and 1007 may be motions in a walking cycle of the left leg.

The walking motion 1001 may correspond to the right hip joint stance phase 1010, and the walking motion 1003 may correspond to the left hip joint swing phase 1020. The walking motion 1005 may correspond to the right ankle push-off phase 1030, and the walking motion 1007 may correspond to the left hip joint stance phase 1040.

A "swing phase" refers to a state of a first leg moving a predetermined angle forward in a walking cycle. A "stance phase" refers to a state of the first leg being in contact with the ground and supporting a body in the walking cycle. For example, a swing phase torque may correspond to a flexion torque in a direction in which a joint bends, and a stance phase torque may correspond to an extension torque in a direction in which a joint stretches.

During a walking, an ankle of a user may perform a dorsi-flexion motion or a plantar-flexion motion about an ankle joint. The dorsi-flexion motion may correspond to a motion of pulling the ankle in a direction toward a top of a foot, and the plantar-flexion motion may correspond to a motion of pushing the ankle in a direction toward a heel, that is, a motion of pushing the ground. A "push-off phase" refers to a state of an ankle of a second leg generating a pushing torque after the swing phase of the first leg. A push-off phase torque may correspond to a foot sole plantar flexion torque. In an example, an ankle joint may be controlled in view of the push-off phase performed in response to the dorsi-flexion motion.

According to a walking mechanism, a walking state when a walking is initiated may differ. However, walking phases including motions of hip joints and ankle joints may transition, for example, in an order of the right hip joint stance phase 1010, the left hip joint swing phase 1020, the right ankle push-off phase 1030, the left hip joint stance phase 1040, the right hip joint swing phase 1050, and the left ankle push-off phase 1060. The walking phases may also be referred to as "walking states."

In an example, the control apparatus (e.g., the controller 140) may recognize a swing phase, a stance phase, and a push-off phase in the following manner.

For example, if pressures measured by pressure sensors are less than or equal to a desired (or, alternatively, a preset) pressure, the control apparatus may determine that a walking state of a user is a swing phase. In this example, the pressure sensors may be positioned at significant portions at which a sole of a foot of the user presses a shoe insole. The pressure sensors may include a forefoot sensor configured to sense a pressure at a ball of the foot of the user, and a rearfoot sensor configured to sense a pressure at a heel of the user.

If the pressures measured by the pressure sensors exceed the desired (or, alternatively, the preset) pressure, the control apparatus (e.g., the controller 140) may determine that the walking state of the user is a stance phase.

In response to determining that the walking state of the user is a stance phase, the control apparatus (e.g., the controller 140) may determine whether the user is to perform a push-off motion based on the pressures measured by the forefoot sensor and the rearfoot sensor. In response to determining that the user is to perform the push-off motion, the control apparatus (e.g., the controller 140) may adjust a torque to assist a push-off phase at an appropriate point in time.

Figure 11:
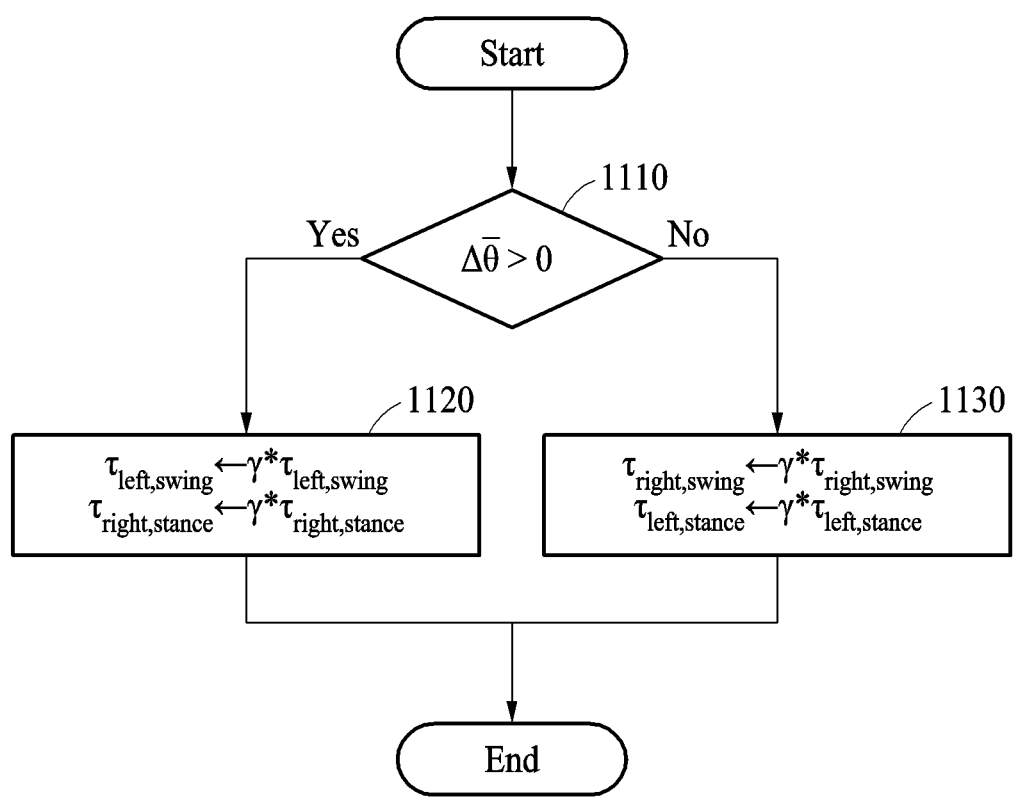
FIGS. 11 through 14 are flowcharts illustrating examples of adjusting a control parameter according to at least one example embodiment.

FIG. 11 is a flowchart illustrating an example of adjusting a control parameter according to at least one example embodiment.

As described above, for a smooth turning walking, a step length of a left leg may decrease during a left turning walking, and a step length of a right leg may decrease during a right turning walking. A control apparatus (e.g., the controller 140) may recognize a turning direction of a user during a turning walking and adjust control parameters based on the turning direction.

When the turning direction of the user is recognized as left, the control apparatus (e.g., the controller 140) may reduce a left step length to easily perform the turning walking. Further, when the turning direction of the user is recognized as right, the control apparatus (e.g., the controller 140) may reduce a right step length to easily perform the turning walking.

To reduce the left step length, the control apparatus (e.g., the controller 140) may reduce a swing phase torque of a left hip joint, and/or reduce a stance phase torque of a right hip joint. To reduce the right step length, the control apparatus (e.g., the controller 140) may reversely perform the operation of reducing the left step length. For example, the control apparatus may reduce a magnitude of the torque by multiplying the torque by a gain.

The control operation with respect to the left and right hip joints of the user for the turning walking may be arranged as shown in Table 1.

TABLE 1

| Hip joint | Left leg | Right leg |
| --- | --- | --- |
| Reduce left step length | Reduce swing phase torque | Reduce stance phase torque |
| Reduce right step length | Reduce stance phase torque | Reduce swing phase torque |

Referring to FIG. 11, in operation 1110, the control apparatus (e.g., the controller 140) may determine whether a variance in a representative component or a variance in a variable component satisfies $\Delta \bar{\theta}_t > 0$. The control apparatus may recognize a turning direction based on a z-axial rotation angle of a body part from which sensor information is obtained. For example, if $\Delta \bar{\theta}_t > 0$, the control apparatus may recognize the turning direction as left. If $\Delta \bar{\theta}_t \leq 0$, the control apparatus may recognize the turning direction as right.

In response to determining that the turning direction is left, that is, $\Delta \bar{\theta}_t > 0$, in operation 1120, the control apparatus (e.g., the controller 140) may reduce a swing phase torque $\tau_{left,swing}$ of a left hip joint of a user and/or reduce a stance phase torque $\tau_{right,stance}$ of a right hip joint of the user by applying a gain $\gamma$.

In response to determining that the turning direction is right, that is, $\Delta \bar{\theta}_t \leq 0$, in operation 1130, the control apparatus (e.g., the controller 140) may reduce a swing phase torque $\tau_{right,swing}$ of the right hip joint of the user and/or reduce a stance phase torque $\tau_{left,stance}$ of the left hip joint of the user by applying the gain $\gamma$.

Here, the gain $\gamma$ may be used to reduce a step length of a turning direction. A gain to be used to reduce the swing phase torques of the left/right hip joints may be equal to or different from a gain to be used to reduce the stance phase torques of the left/right hip joints.

Figure 12:
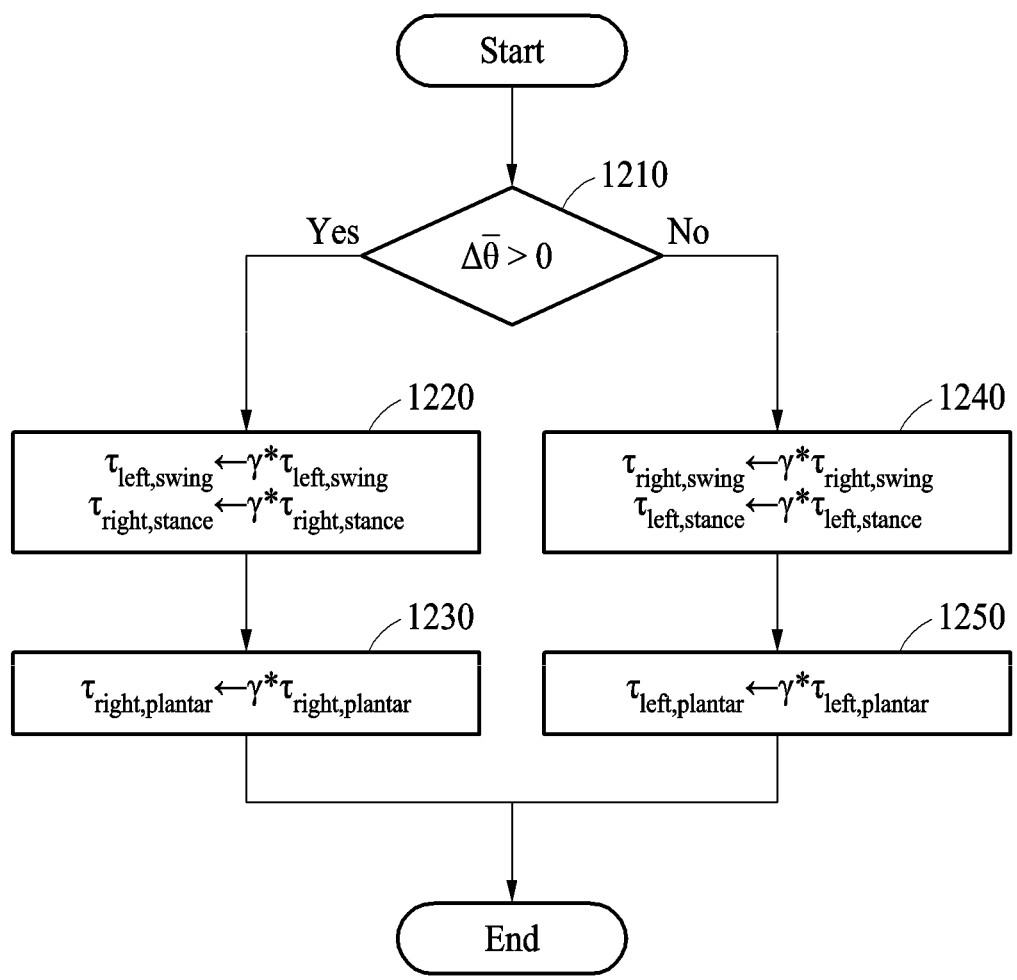

FIG. 12 is a flowchart illustrating an example of adjusting a control parameter according to at least one example embodiment.

In a case of reducing a left step length, the control apparatus may reduce a step length of a left hip joint by reducing a push-off phase torque of an ankle joint of a right leg supporting a body, that is, the right ankle joint. Further, in a case of reducing a right step length, the control apparatus may reduce a step length of a right hip joint by reducing a push-off phase torque of an ankle joint of a left leg, that is, the left ankle joint. The control operation with respect to the left and right ankle joints of a user for a turning walking may be arranged as shown in Table 2.

TABLE 2

| Ankle joint | Left leg | Right leg |
| --- | --- | --- |
| Reduce left step length | X | Reduce push-off phase torque |
| Reduce right step length | Reduce push-off phase torque | X |

To assist the turning walking, the control apparatus may adjust a hip joint torque for each walking phase and an ankle joint torque for each walking phase together, as shown in FIG. 12.

Referring to FIG. 12, in operation 1210, the control apparatus (e.g., the controller 140) may determine whether a variance in a representative component or a variance in a variable component satisfies $\Delta \overline{\theta}_i > 0$. For example, if $\Delta \overline{\theta}_i > 0$, the control apparatus may recognize a turning direction as left. If $\Delta \overline{\theta}_i \leq 0$, the control apparatus may recognize the turning direction as right.

In response to determining that the turning direction is left, that is, $\Delta \overline{\theta}_i > 0$, in operation 1220, the control apparatus (e.g., the controller 140) may reduce a swing phase torque $\tau_{left,swing}$ of a left hip joint of a user and/or reduce a stance phase torque $\tau_{right,stance}$ of a right hip joint of the user by applying a gain γ. In operation 1230, the control apparatus (e.g., the controller 140) may reduce a push-off phase torque $\tau_{right,plantar}$ of a right ankle joint of the user by applying the gain γ.

In response to determining that the turning direction is right, $\Delta \overline{\theta}_i \leq 0$, in operation 1240, the control apparatus (e.g., the controller 140) may reduce a swing phase torque $\tau_{right,swing}$ of the right hip joint of the user and/or reduce a stance phase torque $\tau_{left,stance}$ of the left hip joint of the user by applying the gain γ. In operation 1250, the control apparatus (e.g., the controller 140) may reduce a push-off phase torque $\tau_{left,plantar}$ of a left ankle joint of the user by applying the gain γ.

Here, the gain γ may be used to reduce a step length of a turning direction. A gain to be used to reduce the stance phase torques of the left/right hip joints, a gain to be used to reduce the swing phase torques of the left/right hip joints, and a gain to be used to reduce the push-off phase torques of the left/right ankle joints may be equal to or different from each other.

In an example, a method of controlling a torque for each walking phase of the hip joints and the ankle joints of the left and right legs to reduce a left or right step length may be arranged as shown in Table 3.

TABLE 3

|  |  | Reduce right step length | Reduce left step length |
| --- | --- | --- | --- |
| Left leg | Hip joint | Reduce stance phase torque | Reduce swing phase torque |
|  | Ankle joint | Reduce push-off phase torque |  |

TABLE 3-continued

|  |  | Reduce right step length | Reduce left step length |
| --- | --- | --- | --- |
| Right leg | Hip joint | Reduce swing phase torque | Reduce stance phase torque |
|  | Ankle joint |  | Reduce push-off phase torque |

A relationship among the gain and the torques of the left and right joints in a case of adjusting the control parameter for a left turning walking based on the example of FIG. 12 will be described with reference to FIG. 15.

Figure 13:
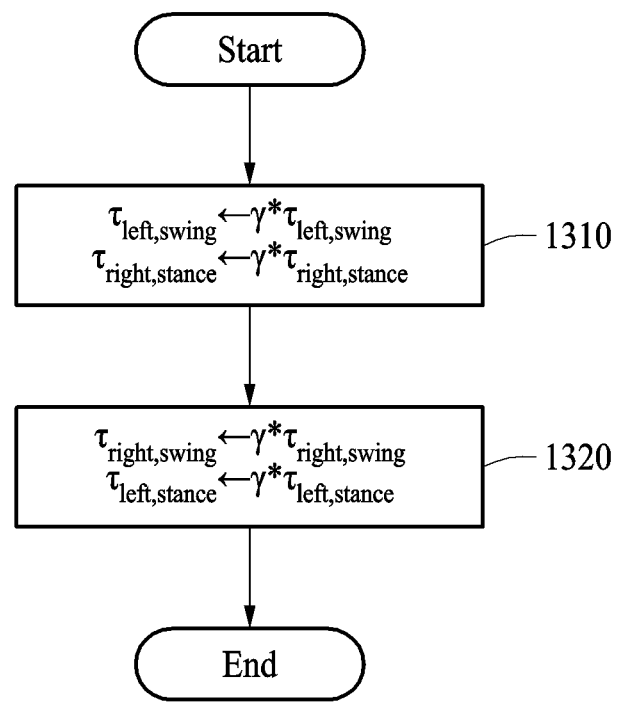

FIG. 13 is a flowchart illustrating an example of adjusting a control parameter according to at least one example embodiment. In general, during a turning walking, a walking speed and a step length decrease in comparison to a straight walking. Reflecting the foregoing, the control apparatus may reduce a torque by multiplying all control parameters by a gain for each turning walking.

Referring to FIG. 13, in operation 1310, the control apparatus (e.g., the controller 140) may reduce a swing phase torque $\tau_{left,swing}$ of a left hip joint of a user and/or reduce a stance phase torque $\tau_{right,stance}$ of a right hip joint of the user by applying a gain γ, in response to recognition of a turning walking of the user.

In operation 1320, the control apparatus (e.g., the controller 140) may reduce a swing phase torque $\tau_{right,swing}$ of the right hip joint of the user and/or reduce a stance phase torque $\tau_{left,stance}$ of the left hip joint of the user by applying the gain γ.

A relationship among the gain and the torques of the left and right joints in a case of adjusting the control parameter for a left turning walking based on the example of FIG. 13 will be described with reference to FIG. 16.

Figure 14:
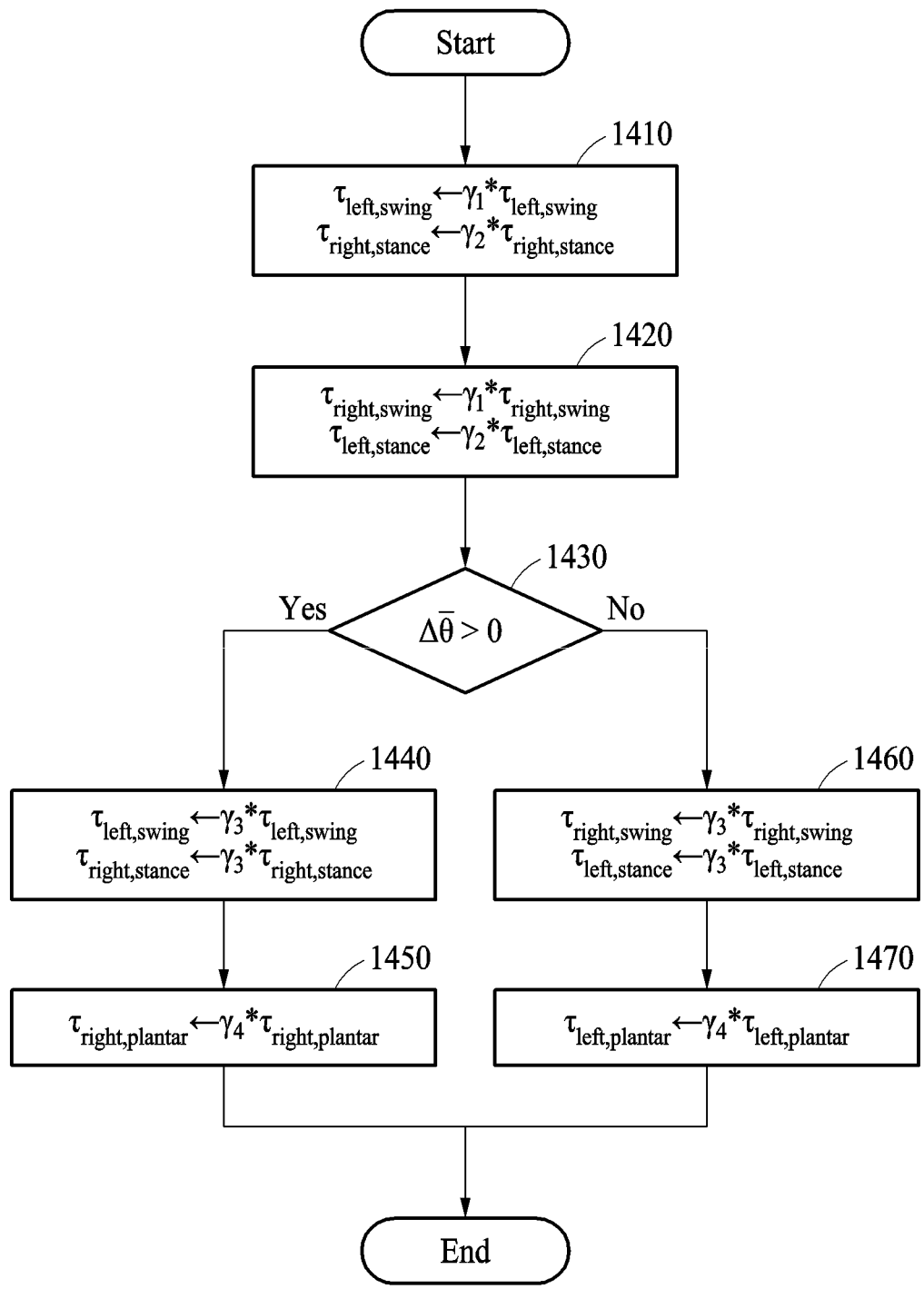

FIG. 14 is a flowchart illustrating an example of adjusting a control parameter according to at least one example embodiment.

Referring to FIG. 14, in operation 1410, the control apparatus (e.g., the controller 140) may reduce a swing phase torque $\tau_{left,swing}$ of a left hip joint of a user by applying a gain $\gamma_1$, and/or reduce a stance phase torque $\tau_{right,stance}$ of a right hip joint of the user by applying a gain $\gamma_2$ in response to recognition of a turning walking of the user.

In operation 1420, the control apparatus (e.g., the controller 140) may reduce a swing phase torque $\tau_{right,swing}$ of the right hip joint of the user by applying the gain $\gamma_1$, and/or reduce a stance phase torque $\tau_{left,stance}$ of the left hip joint of the user by applying the gain $\gamma_2$.

Here, the gain $\gamma_1$ and the gain $\gamma_2$ may be used to reduce an overall speed during the turning walking, and may be, for example, "0.8".

In operation 1430, the control apparatus (e.g., the controller 140) may determine whether a variance in a representative component or a variance in a variable component satisfies $\Delta \overline{\theta}_i > 0$. For example, if $\Delta \overline{\theta}_i > 0$, the control apparatus may recognize a turning direction as left. If $\Delta \overline{\theta}_i \leq 0$, the control apparatus may recognize the turning direction as right.

In response to determining that the turning direction is left, that is, $\Delta \overline{\theta}_i > 0$, the control apparatus (e.g., the controller 140) may reduce the swing phase torque $\tau_{left,swing}$ of the left hip joint of the user and/or reduce the stance phase torque $\tau_{right,stance}$ of the right hip joint of the user by applying a gain $\gamma_3$, in operation 1440. In operation 1450, the control apparatus (e.g., the controller 140) may reduce a push-off phase torque $\tau_{right,plantar}$ of a right ankle joint of the user by applying a gain $\gamma_4$.

In response to determining that the turning direction is right, that is, $\Delta\bar{\theta}_t \leq 0$, the control apparatus (e.g., the controller 140) may reduce the swing phase torque $\tau_{right,swing}$ of the right hip joint of the user and reduce the stance phase torque $\tau_{left,stance}$ of the left hip joint of the user by applying the gain $\gamma_3$, in operation 1460. In operation 1470, the control apparatus (e.g., the controller 140) may reduce a push-off phase torque $\tau_{left,plantar}$ of a left ankle joint of the user by applying the gain $\gamma_4$.

The gain $\gamma_3$ and the gain $\gamma_4$ may be used to reduce a step length of a turning direction, and may be, for example, "0.6".

Figure 15:
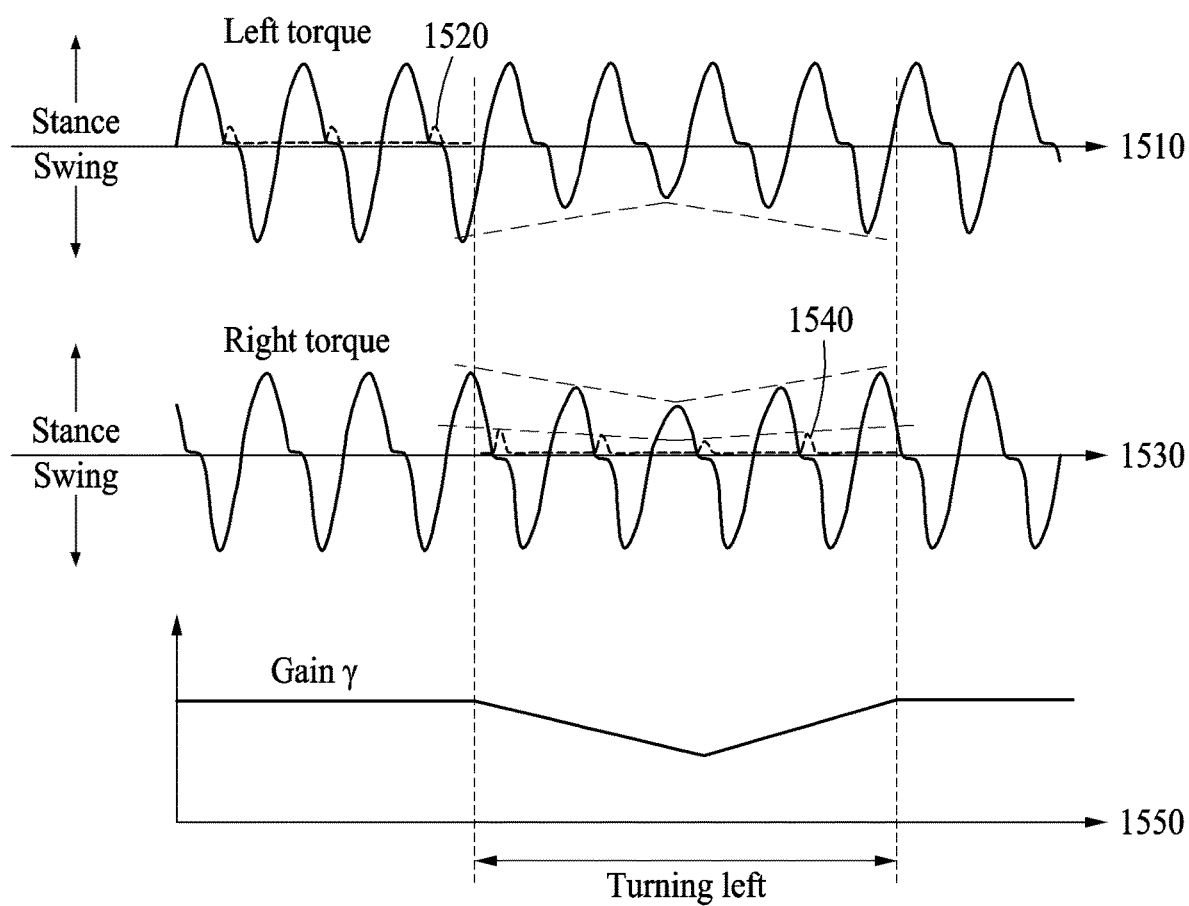
FIGS. 15 and 16 illustrate relationships among a gain and torques of left and right joints during a left turning walking according to at least one example embodiment.

FIG. 15 illustrates a relationship among a gain and torques of left and right joints during a left turning walking according to at least one example embodiment.

Referring to FIG. 15, a relationship among a gain and torques of left and right joints in a case of adjusting a control parameter for a left turning walking based on the example of FIG. 12 is illustrated.

A graph 1510 shows a swing phase torque and a stance phase torque of a left hip joint of a user, and a graph 1520 shows a push-off phase torque of a left ankle joint of the user during a straight walking. In addition, a graph 1530 shows a swing phase torque and a stance phase torque of a right hip joint of the user, and a graph 1540 shows a push-off phase torque of a right ankle joint of the user during a turning walking. A graph 1550 shows a change in a gain in response to a walking of the user.

For example, in a case in which the user performs a straight walking, the control apparatus (e.g., the controller 140) may maintain level of the gain. Thus, the torques shown in the graphs 1510 through 1540 may be the same values having constancy in response to a transition of a walking cycle or a walking phase.

As shown in the graph 1550, the control apparatus (e.g., the controller 140) may gradually reduce the gain in a left turning period marked using broken lines. In this example, the control apparatus may gradually reduce the swing phase torque of the left hip joint as indicated using a broken line on a lower side of the graph 1510. In addition, the control apparatus may gradually reduce the stance phase torque of the right hip joint as indicated using a broken line on an upper side of the graph 1530, and also reduce the push-off phase torque of the right ankle joint as indicated using a broken line on an upper side of the graph 1540, thereby enabling the user to perform a smooth left turning walking.

The control apparatus may gradually reduce a decrement in the gain in response to gradually entering a straight walking period from the turning walking period, thereby adjusting the torques to be suitable for a walking in the straight period.

Figure 16:
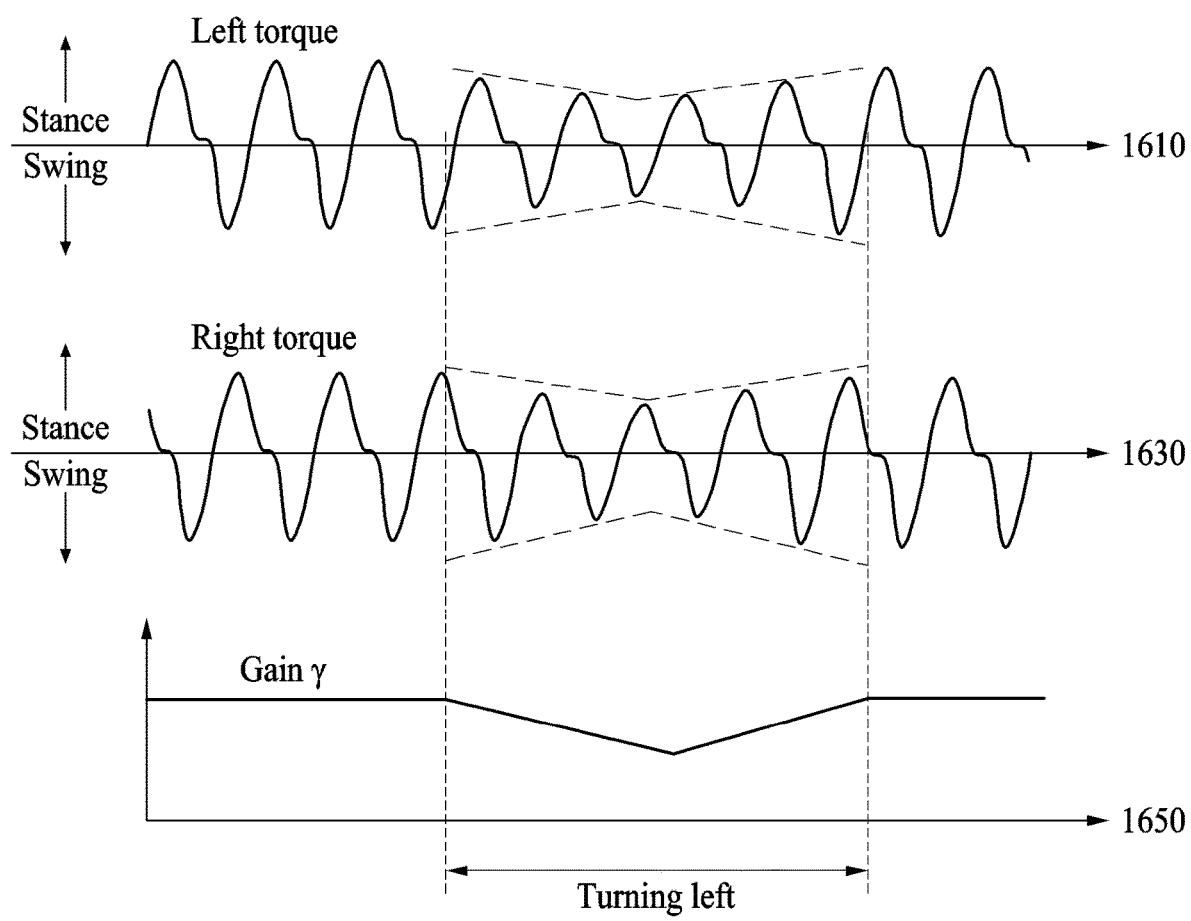

FIG. 16 illustrates a relationship among a gain and torques of left and right joints during a left turning walking according to at least one example embodiment. Referring to FIG. 16, a relationship among a gain and torques of left and right joints in a case of adjusting a control parameter for a left turning walking based on the example of FIG. 13 is illustrated.

A graph 1610 shows a swing phase torque and a stance phase torque of a left hip joint of a user, and a graph 1630 shows a swing phase torque and a stance phase torque of a right hip joint of the user. A graph 1650 shows a change in a gain in response to a walking of the user.

For example, in a case in which the user performs a straight walking, the control apparatus (e.g., the controller 140) may maintain a level of the gain. Thus, the torques shown in the graphs 1610 and 1630 may be the same values having constancy in response to a transition of a walking cycle or a walking phase.

On the contrary, as shown in the graph 1650, the control apparatus (e.g., the controller 140) may gradually reduce the gain in a left turning walking period marked using broken lines. In this example, the control apparatus may gradually reduce the stance phase torque and the swing phase torque of the left hip joint as indicated using broken lines on an upper side and a lower side of the graph 1610. In addition, the control apparatus (e.g., the controller 140) may gradually reduce the stance phase torque and the swing phase torque of the right hip joint as indicated using broken lines on an upper side and a lower side of the graph 1630.

The control apparatus may reduce an overall walking speed by reducing a torque for each walking phase of all joints in a turning walking period, thereby adjusting torques to enable a smooth walking in the turning walking period.

The control apparatus (e.g., the controller 140) may gradually reduce a decrement in the gain in response to gradually entering a straight walking period from the turning walking period, thereby adjusting the torques to be suitable for a walking in the straight period.

Figure 17:
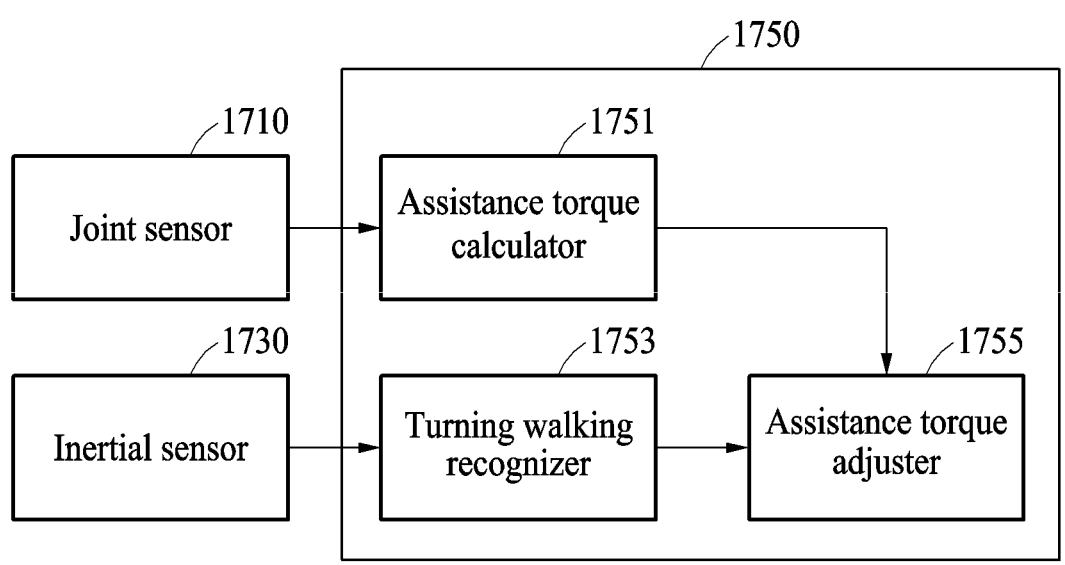
FIGS. 17 and 18 are block diagrams illustrating control apparatuses for a turning walking according to at least one example embodiment.

FIG. 17 is a block diagram illustrating a control apparatus for a turning walking according to at least one example embodiment.

Referring to FIG. 17, a control apparatus 1700 may include a joint sensor 1710, an inertial sensor 1730, and processing circuitry 1750.

The joint sensor 1710 may include a joint angle sensor configured to measure an angle and/or an angular velocity of a joint of a user. For example, the joint of the user may include a hip joint, a knee joint, and an ankle joint. The joint angle sensor may include a hip joint angle sensor, a knee joint angle sensor, and an ankle joint angle sensor.

The inertial sensor 1730 may sense tri-directional, for example, X-axial, Y-axial and Z-axial, accelerations and rotation rates, and tri-directional, for example, roll, pitch and yaw, tilt angles with respect to a walking motion of the user. The inertial sensor 1730 may measure a direction that a torso of the user faces, that is, an orientation of the torso of the user, through a yaw angle.

The processing circuitry 1750 may be included in, for example, the controller 140.

The processing circuitry 1750 may be, but not limited to, a processor, Central Processing Unit (CPU), a controller, an arithmetic logic unit (ALU), a digital signal processor, a microcomputer, a field programmable gate array (FPGA), an Application Specific Integrated Circuit (ASIC), a System-on-Chip (SoC), a programmable logic unit, a microprocessor, or any other device capable of performing operations in a defined manner.

The processing circuitry 1750 may be configured, through a layout design or execution of computer readable instructions stored in a memory (not shown), as a special purpose computer to perform the functions of an assistance torque calculator 1751, a turning walking recognizer 1753, and an assistance torque adjuster 1755.

The assistance torque calculator 1751 may measure a joint angle of the user and calculate a torque to assist a walking of the user based on the joint angle. Further, the assistance torque calculator 1751 may obtain a walking cycle based on the joint angle and/or a transition among a desired (or, alternatively, a predetermined) number of walking states, and calculate the torque based on the walking cycle.

The turning walking recognizer 1753 may recognize a turning walking of the user based on sensor information collected by the joint sensor 1710 and the inertial sensor 1730.

The turning walking recognizer 1753 may track a variable component that varies in response to a walking, based on the sensor information, and determine whether the user is performing a turning walking based on the variable component. The turning walking recognizer 1753 may extract a representative component from the variable component, and determine whether a variance in the representative component is maintained within a desired (or, alternatively, a predetermined) range. In response to determining that the variance exceeds the desired (or, alternatively, the predetermined) range, the turning walking recognizer 1753 may determine that the user is performing a turning walking.

In another example, the turning walking recognizer 1753 may determine whether a variance in a first variable component corresponding to a motion of a left hip joint of the user and a variance in a second variable component corresponding to a motion of a right hip joint of the user is symmetric. In response to determining that the variance in the first variable component and the variance in the second variable component are asymmetric, the turning walking recognizer 1753 may determine that the user is performing a turning walking.

The turning walking recognizer 1753 may recognize a turning degree of the user based on the sensor information. In this example, the assistance torque adjuster 1755 may adjust at least one control parameter or a gain for the at least one control parameter based on the turning degree.

To assist a turning walking, the assistance torque adjuster 1755 may determine the gain for the at least one control parameter, and adjust the calculated torque by applying the gain to the at least one control parameter. The control parameter may include, for example, any one or any combination of a hip joint torque for each walking phase, an ankle joint torque for each walking phase, a knee joint torque for each walking phase, and a foot sole torque for each walking phase.

The assistance torque adjuster 1755 may recognize a turning direction of the user based on the sensor information, and adjust the torque by adjusting the at least one control parameter based on the turning direction.

When the turning direction is left, the assistance torque adjuster 1755 may reduce a swing phase torque of a left hip joint of the user, and reduce a stance phase torque of a right hip joint of the user. When the turning direction is right, the assistance torque adjuster 1755 may reduce a stance phase torque of the left hip joint of the user, and reduce a swing phase torque of the right hip joint of the user.

When the turning direction is left, the assistance torque adjuster 1755 may reduce a push-off phase torque of a right ankle joint of the user. When the turning direction is right, the assistance torque adjuster 1755 may reduce a push-off phase torque of a left ankle joint of the user.

Figure 18:
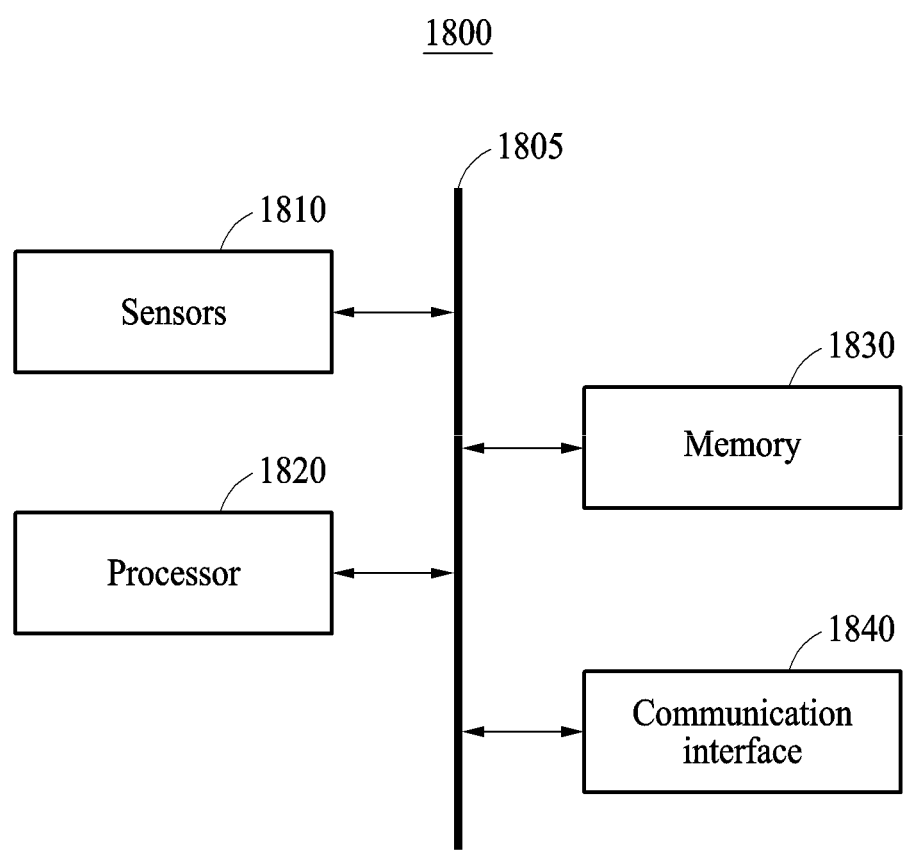

FIG. 18 is a block diagram illustrating a control apparatus for a turning walking according to at least one example embodiment.

Referring to FIG. 18, a control apparatus 1800 may include sensors 1810, a processor 1820, a memory 1830, and a communication interface 1840. The sensors 1810, the processor 1820, the memory 1830, and the communication interface 1840 may communicate with each other through a communication bus 1805.

The sensors 1810 may include various sensors such as a pressure sensor, in addition to the joint sensor 1710 and the inertial sensor 1730 of FIG. 17.

The processor 1820 may recognize a turning walking of a user based on sensor information, and adjust at least one control parameter to assist the turning walking. The processor 1820 may perform all the operations of the processor 1750 of FIG. 17, and also perform the at least one method described with reference to FIGS. 1 through 16 or an algorithm corresponding to the at least one method.

The processor 1820 may be a hardware-implemented data processing device having a circuit with a physical structure to perform desired operations. For example, the desired operations may include codes or instructions included in a program. The hardware-implemented data processing device may include a microprocessor, a central processing unit (CPU), a processor core, a multi-core processor, a multiprocessor, an application-specific integrated circuit (ASIC), and a field programmable gate array (FPGA).

The processor 1820 may execute the program, and control the control apparatus 1800. The codes included in the program executed by the processor 1820 may be stored in the memory 1830.

The memory 1830 may include at least one of a volatile memory, non-volatile memory, random access memory (RAM), a flash memory, a hard disk drive, and an optical disk drive.

The control apparatus 1800 may receive the sensor information through the communication interface 1840. In an example, the communication interface 1840 may receive the sensor information from other sensors existing outside the control apparatus 1800.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such as parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A control method, comprising:
   instructing a driver to output, in different ones of a plurality of walking phases, a rotational torque to a support attached to a user to assist the user with straight walking, the plurality of walking phases including at least a swing phase, a stance phase, and a push-off-phase;
   receiving sensor information while assisting the user with the straight walking;
   recognizing, based on the sensor information, that the user is performing a turning operation in a turning direction while assisting the user with the straight walking through the plurality of walking phases; and
   in response to the user performing the turning operation, adjusting at least one control parameter to assist the turning operation by gradually reducing a gain of the rotational torque associated with at least one of the swing phase, the stance phase, and the push-off-phase from the gain of the rotational torque when walking straight to a value greater than zero to generate a reduced rotational torque that varies during the at least one of the swing phase, the stance phase, and the push-off-phase, and
   instructing the driver to change from outputting the rotational torque to outputting the reduced rotational torque to the support in the at least one of the swing phase, the stance phase, and the push-off-phase to assist the user in performing the turning operation such that, while performing the turning operation, the rotational torque output by the driver varies during the at least one of the swing phase, the stance phase, and the push-off-phase and is reduced as compared to the straight walking.

2. The control method of claim 1, wherein the recognizing comprises:
   tracking a variable component based on the sensor information, the variable component varying in response to the walking; and
   determining whether the user is performing the turning operation based on the variable component.

3. The control method of claim 2, wherein the determining whether the user is performing the turning operation comprises:
   extracting a representative component from the variable component;
   determining whether a variance in the representative component is maintained within a set range; and
   determining that the user is performing the turning operation, if the variance exceeds the set range.

4. The control method of claim 3, wherein the variable component includes one or more of a direction that a body of the user faces during the walking and a direction that a pelvis of the user faces during the walking.

5. The control method of claim 2, wherein the variable component includes a first variable component and a second variable component, the first variable component corresponding to a motion of a left hip joint of the user, and the second variable component corresponding to a motion of a right hip joint of the user, and wherein the determining whether the user is performing the turning operation comprises:
   determining whether a variance in the first variable component and a variance in the second variable component are symmetric; and
   determining that the user is performing the turning operation, if the variance in the first variable component and the variance in the second variable component are asymmetric.

6. The control method of claim 1, wherein the adjusting the at least one control parameter comprises:
   determining the gain of the rotational torque to assist the turning operation; and
   applying the gain to the rotational torque to generate the reduced rotational torque.

7. The control method of claim 1, wherein the at least one control parameter includes one or more of a hip joint torque for each walking phase, an ankle joint torque for each walking phase, a knee joint torque for each walking phase, and a foot sole torque for each walking phase.

8. The control method of claim 1, further comprising:
   recognizing the turning direction associated with the turning operation based on the sensor information, wherein
   the adjusting the at least one control parameter comprises adjusting the at least one control parameter based on the turning direction.

9. The control method of claim 8, wherein the recognizing the turning direction comprises:
recognizing the turning direction based on a z-axial rotation angle of a body part from which the sensor information is obtained.

10. The control method of claim 8, wherein, when the recognizing the turning direction recognizes the turning direction as a left turn direction, the adjusting of the at least one control parameter based on the turning direction comprises:
reducing a swing phase torque of a left hip joint of the user; and
reducing a stance phase torque of a right hip joint of the user.

11. The control method of claim 8, wherein, when the recognizing the turning direction recognizes the turning direction as a right turn direction, the adjusting of the at least one control parameter based on the turning direction comprises:
reducing a stance phase torque of a left hip joint of the user; and
reducing a swing phase torque of a right hip joint of the user.

12. The control method of claim 8, wherein, when the recognizing the turning direction recognizes the turning direction as a left turn direction, the adjusting of the at least one control parameter based on the turning direction comprises:
reducing a push-off phase torque of a right ankle joint of the user.

13. The control method of claim 8, wherein, when the recognizing the turning direction recognizes the turning direction as a right turn direction, the adjusting of the at least one control parameter based on the turning direction comprises:
reducing a push-off phase torque of a left ankle joint of the user.

14. The control method of claim 1, further comprising:
recognizing a turning degree of the user based on the sensor information, wherein
the adjusting the at least one control parameter comprises adjusting the at least one control parameter based on the turning degree.

15. The control method of claim 14, wherein the adjusting of the at least one control parameter comprises:
adjusting the gain of the rotational torque based on the turning degree such that the gain gradually decreases as the turning degree increases.

16. The control method of claim 1, wherein the receiving of the sensor information comprises:
receiving the sensor information from one or more of an inertial sensor, an azimuth sensor, a geomagnetic sensor, and a foot sole contact sensor.

17. A non-transitory computer-readable medium comprising computer readable instructions to cause a computer to perform the control method of claim 1.

18. A walking assistance apparatus, comprising:
a support configured to attach to a limb of a user;
a driver; and
a control apparatus including,
a communication interface configured to receive sensor information; and
a processor configured to,
instruct the driver to output, in different ones of a plurality of walking phases, a rotational torque to the support attached to the limb of the user to assist the user with straight walking, the plurality of walking phases including at least a swing phase, a stance phase, and a push-off-phase,
recognize, based on the sensor information, that the user is performing a turning operation in a turning direction while assisting the user with the straight walking through the plurality of walking phases, and
in response to the user performing the turning operation,
adjusting at least one control parameter to assist the turning operation by gradually reducing a gain of the rotational torque associated with at least one of the swing phase, the stance phase, and the push-off-phase from the gain of the rotational torque when walking straight to a value greater than zero to generate a reduced rotational torque that varies during the at least one of the swing phase, the stance phase, and the push-off-phase, and
instructing the driver to change from outputting the rotational torque to outputting the reduced rotational torque to the support in the at least one of the swing phase, the stance phase, and the push-off-phase to assist the user in performing the turning operation such that, while performing the turning operation, the rotational torque output by the driver varies during the at least one of the swing phase, the stance phase, and the push-off-phase and is reduced as compared to the straight walking.

19. The walking assistance apparatus of claim 18, wherein the processor is configured to,
track a variable component based on the sensor information, the variable component varying in response to the walking, and
determine whether the user is performing the turning operation based on the variable component.

20. The walking assistance apparatus of claim 19, wherein the processor is configured to,
extract a representative component from the variable component,
determine whether a variance in the representative component is maintained within a set range, and
determine that the user is performing the turning operation, if the variance exceeds the set range.

21. The walking assistance apparatus of claim 20, wherein the variable component includes one or more of a direction that a body of the user faces during the walking and a direction that a pelvis of the user faces during the walking.

22. The walking assistance apparatus of claim 19, wherein the variable component includes a first variable component and a second variable component, the first variable component corresponding to a motion of a left hip joint of the user, and the second variable component corresponding to a motion of a right hip joint of the user, and wherein the processor is configured to,
determine whether a variance in the first variable component and a variance in the second variable component are symmetric, and
determine that the user is performing the turning operation, if the variance in the first variable component and the variance in the second variable component are asymmetric.

23. The walking assistance apparatus of claim 18, wherein the processor is configured to,
determine the gain of the rotational torque to assist the turning operation, and apply the gain to the rotational torque to generate the reduced rotational torque.

24. The walking assistance apparatus of claim 18, wherein the at least one control parameter includes one or more of a hip joint torque for each walking phase, an ankle joint torque for each walking phase, a knee joint torque for each walking phase, and a foot sole torque for each walking phase.

25. The walking assistance apparatus of claim 18, wherein the processor is configured to,
    recognize the turning direction associated with the turning operation based on the sensor information, and
    adjust the at least one control parameter based on the turning direction.

26. The walking assistance apparatus of claim 25, wherein the processor is configured to recognize the turning direction based on a z-axial rotation angle of a body part from which the sensor information is obtained.

27. The walking assistance apparatus of claim 25, wherein the processor is configured to, when the turning direction is left,
    reduce a swing phase torque of a left hip joint of the user, and
    reduce a stance phase torque of a right hip joint of the user.

28. The walking assistance apparatus of claim 25, wherein the processor is configured to, when the turning direction is right,
    reduce a stance phase torque of a left hip joint of the user, and
    reduce a swing phase torque of a right hip joint of the user.

29. The walking assistance apparatus of claim 25, wherein the processor is configured to, when the turning direction is left, reduce a push-off phase torque of a right ankle joint of the user.

30. The walking assistance apparatus of claim 25, wherein the processor is configured to, when the turning direction is right, reduce a push-off phase torque of a left ankle joint of the user.

31. The walking assistance apparatus of claim 18, wherein the processor is configured to,
    recognize a turning degree of the user based on the sensor information, and
    adjust the at least one control parameter based on the turning degree.

32. The walking assistance apparatus of claim 31, wherein the processor is configured to adjust the gain for the rotational torque based on the turning degree such that the gain gradually decreases as the turning degree increases.

33. The walking assistance apparatus of claim 18, wherein the communication interface is configured to receive the sensor information from one or more of an inertial sensor, an azimuth sensor, a geomagnetic sensor, and a foot sole contact sensor.

34. The control method of claim 1, wherein the adjusting of the at least one control parameter to assist the turning operation comprises:
    gradually reducing a push-off phase torque associated with the push-off phase of an ankle joint of a leg opposite a turning direction of the user, in response to the user performing the turning operation in the turning direction.

35. The walking assistance apparatus of claim 18, wherein the processor is configured to adjust the at least one control parameter to assist the turning operation by gradually reducing a push-off phase torque associated with the push-off phase of an ankle joint of a leg opposite a turning direction of the user, in response to the user performing the turning operation in the turning direction.

* * * * *